(12) United States Patent
Potyrailo et al.

(10) Patent No.: US 9,689,852 B2
(45) Date of Patent: *Jun. 27, 2017

(54) RESONANT SENSOR AND AN ASSOCIATED SENSING METHOD

(71) Applicant: General Electric Company, Schenectady, NY (US)

(72) Inventors: Radislav Alexandrovich Potyrailo, Niskayuna, NY (US); Yongjae Lee, Latham, NY (US)

(73) Assignee: GENERAL ELECTRIC COMPANY, Niskayuna, NY (US)

( * ) Notice: Subject to any disclaimer, the term of this patent is extended or adjusted under 35 U.S.C. 154(b) by 50 days.

This patent is subject to a terminal disclaimer.

(21) Appl. No.: 15/175,127

(22) Filed: Jun. 7, 2016

(65) Prior Publication Data

US 2016/0290944 A1    Oct. 6, 2016

Related U.S. Application Data

(63) Continuation-in-part of application No. 13/538,570, filed on Jun. 29, 2012.

(51) Int. Cl.
*G01R 33/385* (2006.01)
*H03K 17/955* (2006.01)
(Continued)

(52) U.S. Cl.
CPC ....... *G01N 33/0031* (2013.01); *G01N 27/026* (2013.01); *H05K 1/16* (2013.01);
(Continued)

(58) Field of Classification Search
CPC .............. G01R 33/543; G01R 33/4818; G01R 33/4828; G01R 33/385; G01R 27/26; G01R 27/2605; G01D 5/24; G01D 5/241; G01D 5/2412; G01D 5/2417; G06K 9/0002; H03K 17/955; H03K 2217/960725; G06F 3/0414
USPC ....... 324/655, 309, 315, 316, 633, 652, 668, 324/675, 682, 708, 76.51, 696, 65, 4, 324/658, 661, 663, 519, 548, 662, 669,
(Continued)

(56) References Cited

U.S. PATENT DOCUMENTS

2006/0133720 A1* 6/2006 Hochberg .......... G02B 6/12007
385/15
2008/0280374 A1* 11/2008 Potyrailo ............. G01N 21/554
436/172

(Continued)

*Primary Examiner* — Hoai-An D Nguyen
*Assistant Examiner* — Taqi Nasir
(74) *Attorney, Agent, or Firm* — John P. Darling

(57) ABSTRACT

A sensing system for selective analyte detection in presence of interferences is presented. The sensing system includes an inductor-capacitor-resistor (LCR) resonant sensor includes a substrate, a plurality of first sensing elements mutually spaced apart and disposed on the substrate, a plurality of second sensing elements, each second sensing element disposed overlapping a corresponding first sensing element of the plurality of second sensing elements, and a protecting film applied onto the plurality of first sensing elements and the plurality of second sensing elements, wherein the protecting film is disposed to be in a physical contact with the analyte and is configured to enable an operational contact of the plurality of first sensing elements and the plurality of second sensing elements with the analyte.

19 Claims, 16 Drawing Sheets

(51) Int. Cl.
*G01N 33/00* (2006.01)
*G01N 27/02* (2006.01)
*H05K 1/16* (2006.01)

(52) U.S. Cl.
CPC ........... *H05K 2201/0338* (2013.01); *H05K 2201/09263* (2013.01); *H05K 2201/10151* (2013.01); *Y10T 29/4913* (2015.01)

(58) Field of Classification Search
USPC .......... 324/671, 684, 76.79, 76.81, 12, 3 R, 324/123 C, 750.17
See application file for complete search history.

(56) References Cited

U.S. PATENT DOCUMENTS

| | | | |
|---|---|---|---|
| 2010/0134286 A1* | 6/2010 | Potyrailo | G06K 19/07749 340/572.1 |
| 2010/0268479 A1* | 10/2010 | Potyrailo | G01N 27/026 702/23 |
| 2011/0101996 A1* | 5/2011 | Potyrailo | G01D 21/00 324/655 |
| 2012/0004851 A1* | 1/2012 | Potyrailo | G01N 33/0073 702/19 |
| 2012/0116683 A1* | 5/2012 | Potyrailo | G01N 27/02 702/19 |

* cited by examiner

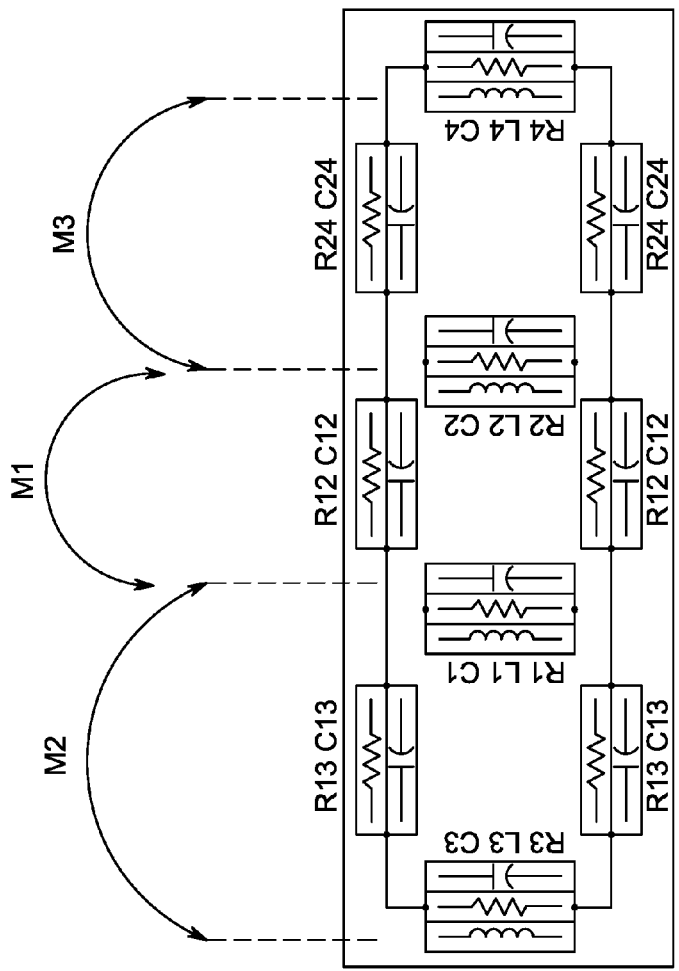
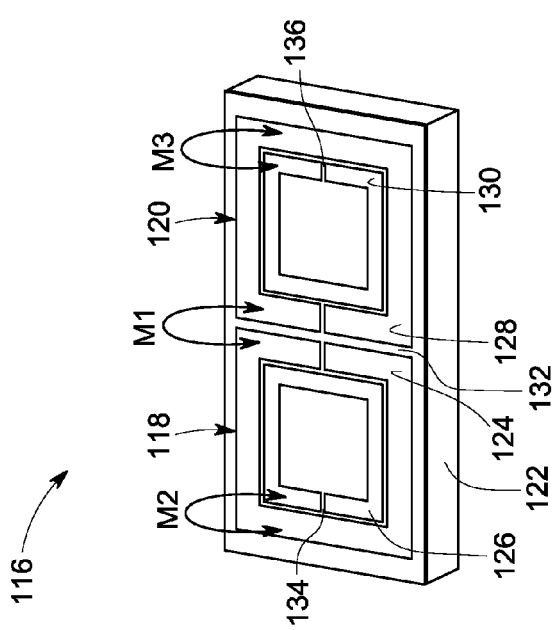
FIG. 22
FIG. 21

RESONANT SENSOR AND AN ASSOCIATED SENSING METHOD

CROSS REFERENCE TO RELATED APPLICATIONS

This application is a continuation-in-part of U.S. patent application Ser. No. 13/538,570 entitled "RESONANT SENSOR AND AN ASSOCIATED SENSING METHOD", filed on Jun. 29, 2012.

BACKGROUND

The invention relates generally to sensing devices and more particularly to inductor-capacitor-resistor (LCR) sensing devices having enhanced selectivity and sensitivity.

Selectivity of sensors is one of the important aspects in sensor performance and applications. Typically, lack of selectivity prevents the wide use of sensors in sensing chemical and biological species in liquids and air for industrial and other applications. Two known approaches to address the problem associated with lack of selectivity include developing very selective sensing films, and combining individual diverse sensors into an array. Unfortunately, each approach suffers from its own limitations. Highly selective sensing films typically have relatively slow recovery times due to strong vapor-material interactions. Combining sensors into an array may have manufacturing challenges.

Chemical and biological detection has been accomplished using radio frequency identification (RFID) sensors. Sensor response originates from changes in dielectric properties of the sensing film deposited onto a sensor. While RFID sensors can detect individual chemical and physical changes based on changes in dielectric properties, there is a need to further improve selectivity of the RFID sensors.

BRIEF DESCRIPTION

In accordance with an exemplary embodiment of the present invention, a sensing system for selective analyte detection in presence of interferences is presented. The sensing system includes an inductor-capacitor-resistor (LCR) resonant sensor includes a substrate, a plurality of first sensing elements mutually spaced apart and disposed on the substrate, a plurality of second sensing elements, each second sensing element disposed overlapping a corresponding first sensing element of the plurality of second sensing elements, and a protecting film applied onto the plurality of first sensing elements and the plurality of second sensing elements, wherein the protecting film is disposed to be in a physical contact with the analyte and is configured to enable an operational contact of the plurality of first sensing elements and the plurality of second sensing elements with the analyte.

In accordance with an exemplary embodiment of the present invention, a method for fabrication of an inductor-capacitor-resistor (LCR) resonant sensor is presented. The method includes applying a plurality of first sensing elements on a substrate, applying at least one dielectric layer on the plurality of first sensing elements, applying a plurality of second sensing elements on the at least one dielectric layer, each second sensing element being disposed corresponding to position of each first sensing element such that the at least one dielectric layer is disposed between the plurality of first and second sensing elements, and applying a protecting film onto the plurality of first sensing elements and the plurality of second sensing elements, wherein the protecting film is disposed to be in a physical contact with an analyte and is configured to enable an operational contact of the plurality of first sensing elements and the plurality of second sensing elements with the analyte.

DRAWINGS

These and other features, aspects, and advantages of the present invention will become better understood when the following detailed description is read with reference to the accompanying drawings in which like characters represent like parts throughout the drawings, wherein:

FIG. 21 is a perspective view of a dual-SRR (split ring resonator) sensor in accordance with an exemplary embodiment of the present invention;

FIG. 22 is a diagrammatical representation of a dual-SRR sensor represented as an L-C-R equivalent circuit in accordance with an exemplary embodiment of FIG. 21;

DETAILED DESCRIPTION

Figure 1:
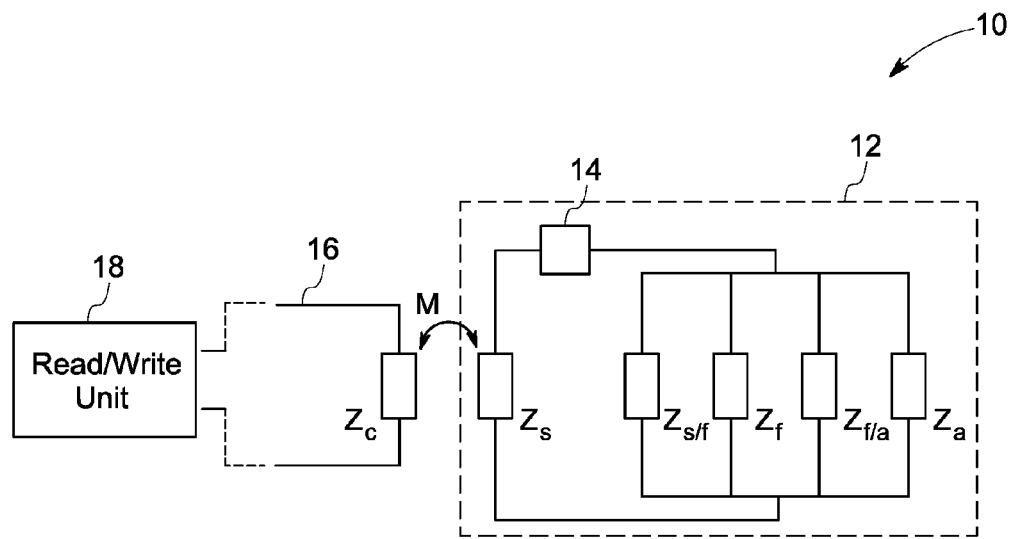
FIG. 1 is a diagrammatical representation of a sensing system, for example RFID sensing system in accordance with an exemplary embodiment of the present invention.

The embodiments of the present invention are related to a sensing system, for example an RFID sensing system for simultaneous sensing of one or more properties of a sample. As used herein, a RFID sensing system includes an inductor-capacitor-resistor (LCR) resonant sensor and an excitation element such as a pick-up coil (detector).

To more clearly and concisely describe the subject matter of the claimed invention, the following definitions are provided for specific terms, which are used in the following description and the appended claims.

The term "fluids" may include gases, vapors, liquids, and solids.

The term "analyte" includes any substance or chemical constituent that is the subject of a chemical or biological analysis. Examples of analytes include, but are not limited to, acidic or basic gases, oxidant or reducing gases, other gases, or any combination thereof. Examples of acidic or basic gases include, but are not limited to ammonia, hydrogen sulfide, methanethiol, hydrogen bromide, hydrogen chloride, hydrogen iodide, hydrogen fluoride, and so forth. Examples of oxidant or reducing gases include, but are not limited to hydrogen peroxide, chlorine dioxide, oxygen, chlorine, bromine, and so forth. Examples of other gases include, but are not limited to sulfur dioxide, arsine, hydrogen cyanide, phosgene, triacetone triperoxide, carbon dioxide, carbon monoxide, trinitrotoluene, explosives, and so forth.

The term "digital ID" includes all data stored in a memory chip of the RFID sensor. Non-limiting examples of such data are manufacturer identification, electronic pedigree data, user data, and calibration data for the sensor.

The term "monitoring process" includes, but is not limited to, measuring physical changes that occur around the sensor. For example, monitoring processes including monitoring changes in a biopharmaceutical, food or beverage manufacturing process related to changes in physical, chemical, and/or biological properties of an environment around the sensor. Monitoring processes may also include those industry processes that monitor physical changes as well as changes in a component's composition or position. Non-limiting examples include homeland security monitoring, residential home protection monitoring, environmental monitoring, clinical or bedside patient monitoring, airport security monitoring, admission ticketing, and other public events. Monitoring can be performed when the sensor signal has reached an appreciably steady state response and/or when the sensor has a dynamic response. The steady state sensor response is a response from the sensor over a determined period of time, where the response does not appreciably change over the measurement time. Thus, measurements of steady state sensor response over time produce similar values. The dynamic sensor response is a response from the sensor based upon a change in the measured environmental parameter (for example, temperature, pressure, chemical concentration, biological concentration, or the like). Thus, the dynamic sensor response significantly changes over the measurement time to produce a dynamic signature of response toward the environmental parameter or parameters measured. Non-limiting examples of the dynamic signature of the response include average response slope, average response magnitude, largest positive slope of signal response, largest negative slope of signal response, average change in signal response, maximum positive change in signal response, and maximum negative change in signal response. The produced dynamic signature of response can be used to further enhance the selectivity of the sensor in dynamic measurements of individual vapors and their mixtures. The produced dynamic signature of response can also be used to further optimize the combination of irreversible sensing material and transducer geometry to enhance the selectivity of the sensor in dynamic and steady state measurements of individual vapors and their mixtures.

The term "environmental parameters" is used to refer to measurable environmental variables within or surrounding a manufacturing or monitoring system. The measurable environmental variables include at least one of physical, chemical, and biological properties and include, but are not limited to measurement of temperature, pressure, material concentration, conductivity, dielectric property, number of dielectric, metallic, chemical, or biological particles in the proximity or in contact with the sensor, dose of ionizing radiation, and light intensity. The measurable environmental variables are also of a material in contact with the sensor such as a sensing material or a sensing film.

As used herein the term "sensing materials and sensing films" includes, but is not limited to, materials deposited onto a transducer's electronics module, such as LCR circuit components or an RFID tag, to perform the function of predictably and reproducibly affecting the impedance sensor response upon interaction with the environment. In order to prevent the material in the sensor film from leaking into the liquid environment, the sensing materials are attached to the sensor surface using standard techniques, such as covalent bonding, electrostatic bonding, and other standard techniques known to those of ordinary skill in the art.

The term "interference" includes any undesired environmental parameter that undesirably affects the accuracy and precision of measurements of the sensor. The term "interferent" refers to a fluid or an environmental parameter (that includes, but is not limited to temperature, pressure, light, or the like) that potentially may produce an interference response by the sensor.

The term "multivariate analysis" refers to a mathematical procedure that is used to analyze more than one variable from the sensor response and to provide the information about the type of at least one environmental parameter from the measured sensor spectral parameters and/or to quantitative information about the level of at least one environmental parameter from the measured sensor spectral parameters. The term "principal components analysis (PCA)" refers to a mathematical procedure that is used to reduce multidimensional data sets to lower dimensions for analysis. Principal components analysis is a part of Eigen analysis methods of statistical analysis of multivariate data and may be performed using a covariance matrix or correlation matrix. Non-limiting examples of multivariate analysis tools include canonical correlation analysis, regression analysis, nonlinear regression analysis, principal components analysis, discriminate function analysis, multidimensional scaling, linear discriminate analysis, logistic regression, or neural network analysis.

The term "multivariate sensor" is referred to herein as a single sensor capable of producing a plurality of response signals that are not substantially correlated with each other. These individual response signals from the multivariate sensor are further analyzed using one or more multivariate analysis tools to contrast the response patterns of exposures to different analytes and the different analyte concentrations. In one embodiment, multivariable or multivariate signal transduction is performed on the plurality of response signals using the one or more multivariate analysis tools to construct a multivariate sensor response pattern.

The term "spectral parameters" is used to refer to measurable variables of the sensor response. The sensor response is the impedance spectrum of the resonance sensor circuit of the LCR or RFID sensor. In addition to measuring the impedance spectrum in the form of Z-parameters, S-parameters, and other parameters, the impedance spectrum may be analyzed simultaneously using various parameters for analysis, such as the frequency of the maximum of the real part of the impedance ($F_p$), the peak magnitude of the real part of the impedance ($Z_p$), the first peak frequency of the imaginary part of the impedance ($F_1$), the second valley frequency of the imaginary part of the impedance ($F_2$), signal magnitude ($Z_1$) at the peak frequency of the imaginary part of the impedance ($F_1$), signal magnitude ($Z_2$) at the second resonant frequency of the imaginary part of the impedance ($F_2$), and zero-reactance frequency ($F_z$), frequency at which the imaginary portion of impedance is zero. Other spectral parameters may be simultaneously measured using the entire impedance spectra, for example, quality factor of resonance, phase angle, and magnitude of impedance. Collectively, "spectral parameters" calculated from the impedance spectra, may be referred to as "features" or "descriptors." The appropriate selection of features is performed from all potential features that can be calculated from spectra. Multivariable spectral parameters are described in U.S. Pat. No. 7,911,345 entitled "Methods and systems for calibration of RFID sensors," which is incorporated herein by reference.

The term "resonance impedance" or "impedance" refers to measured sensor frequency response as real and imaginary parts of impedance around the resonance of the sensor from which the sensor "spectral parameters" are extracted.

The terms "transducer" and "sensor" are used to refer to electronic devices such as RFID and LCR devices intended for sensing. "Transducer" is a device before it is coated with a sensing or protecting film or before it is calibrated for a sensing application. "Sensor" is a device typically after it is coated with a sensing or protecting film and after being calibrated for the sensing application.

As used herein the term "RFID tag" refers to an identification and reporting technology that uses electronic tags for identifying and/or tracking articles to which the RFID tag may be attached. An RFID tag typically includes at least two components where the first component is an integrated circuit (IC) memory chip for storing and processing information, and modulating and demodulating a radio frequency signal. The memory chip can also be used for other specialized functions, for example, the chip may contain a capacitor. The chip may also contain at least one input for an analog signal such as a resistance input, capacitance input, or inductance input. In the case of a chipless RFID tag, the RFID tag may not include an IC memory chip. Such an RFID tag may be useful in applications where a specific RFID tag does not need to be identified, but rather a signal merely indicating the presence of the tag that provides useful information (e.g., product security applications). The second component of the RFID tag is an antenna for receiving and transmitting the radio frequency signal.

The term "RFID sensor" is an RFID tag with an added sensing function as, for example, when an antenna of the RFID tag also performs sensing functions by changing its impedance parameters as a function of environmental changes. The accurate determinations of environmental changes using such RFID sensors are performed by analysis of resonance impedance. For example, RFID tags may be converted into RFID sensors by coating the RFID tag with a sensing film. By coating the RFID tag with a sensing film, the electrical response of the film is translated into simultaneous changes to the impedance response, resonance peak position, peak width, peak height and peak symmetry of the impedance response of the sensor antenna, magnitude of the real part of the impedance, resonant frequency of the imaginary part of the impedance, anti-resonant frequency of the imaginary part of the impedance, zero-reactance frequency, phase angle, and magnitude of impedance, and others as described in the definition of the term sensor "spectral parameters." The "RFID sensor" may have an integrated circuit (IC) memory chip attached to the antenna or may have no IC memory chip. An RFID sensor without an IC memory chip is an LCR sensor. An LCR sensor includes components, such as at least one inductor (L), at least one capacitor (C), and at least one resistor (R) to form an LCR circuit.

The term "writer/reader" includes, but is not limited to, a combination of devices to write and read data into the memory of the memory chip and to read impedance of the antenna. The term "writer/reader" may also be referred to as an "interrogator."

In accordance with embodiments disclosed herein, an LCR or an RFID sensor for sensing vapors, vapor mixtures, and biological species is described. As previously described, the RFID sensor includes an RFID tag coated with an irreversible sensing material. In one embodiment, a passive RFID tag may be employed. As will be appreciated, an RFID tag may include an IC memory chip, which is connected to an antenna coil for communication with a writer/reader. The IC memory chip can be read by illuminating the tag by a radio frequency (RF) and/or microwave carrier signal sent by the writer/reader. When the RF and/or microwave field passes through the antenna coil, an AC voltage is generated across the coil. The voltage is rectified in the microchip to result in a DC voltage for the microchip operation. The IC memory chip becomes functional when the DC voltage reaches a predetermined level. By detecting the RF and/or microwave signal backscattered from the microchip, the information stored in the microchip can be fully identified. The distance between the RFID tag/sensor and the writer/reader is governed by the design parameters that include operating frequency, RF and/or microwave power level, the receiving sensitivity of the reader/writer, antenna dimensions, data rate, communication protocol, and microchip power requirements. The distance between the "RFID sensor" without an IC memory chip (chipless RFID sensor or LCR sensor or LCR transducer) and the sensor reader is governed by the design parameters that include operating frequency, RF or microwave power level, the receiving sensitivity of the sensor reader, and antenna dimensions.

Sensor response originates from changes in dielectric and dimensional properties of a sensing film deposited onto a LCR resonant sensor. Additionally, the sensor response may originate from changes in a dielectric and a dimensional property of a substrate and/or a dielectric isolator of an electrode structure of the LCR resonant sensor. The dielectric and dimensional property of the substrate and/or the dielectric isolator may change due to an interaction of the LCR resonant sensor with the analyte. The change in the dimensional property, for example, may include at least one of swelling, shrinking and bending. For example, the substrate may experience change in the dimensional property and/or the dielectric property upon exposure to the analyte. A change in dimensional property and the dielectric property of the sensing film, the dielectric isolator and/or the substrate are measured by measuring the resonance response of the LCR sensor. The LCR sensor may be used for sensing one or more properties of a sample. Properties may include a physical condition, a biological condition, or a chemical condition and may include a quantitative response for a desired parameter. For example, the sensor may be employed to monitor magnitude of an environmental parameter of interest such as, but not limited to, conductivity measurement, pH level, temperature, blood relevant measurement, ionic measurement, non-ionic measurement, non-conductivity measurement, electromagnetic radiation level measurement, pressure, vapor concentration, biological material concentration, and other types of measurements that may be taken from a typical sample (solution or gas or solid). The selectivity of the LCR resonant sensor is provided by at least three orthogonal responses related to the variation of the sensor inductance, capacitance, and resistance. These orthogonal responses are provided by the combination of the sensor geometry, data acquisition, sensing material of the sensing film, and multivariate data analysis techniques. It should be noted herein that in accordance with the embodiments of the present invention, the LCR resonant sensor may be referred to as "a multivariate sensor".

The multivariate resonant sensor generates a plurality of orthogonal responses defined as the number of orthogonal axes generated after the multivariate analysis that include the analyte-relevant information.

In certain embodiments, the sample may include a container such as a disposable container, a bioreactor, a stainless steel container, a plastic container, a polymeric material container, or a pre-sterilized polymeric material container. Further, the container may be of different size and shape, for example, a micro fluidic channel, a Petri dish, a glove box, a hood, or a plastic bag. The sample can also be an indoor enclosure or an outdoor monitoring station. In certain embodiments, the container is a disposable bioprocess component. Non-limiting examples of the bioprocess component include a disposable storage bag, a disposable container, a product transfer line, a filter, a connector, a valve, a pump, a bioreactor, a separation column, a mixer, or a centrifugation system. In one embodiment, the disposable container or bag may be made of plastic. The disposable container may include ports for inserting the LCR resonant sensor and the pick-up coil. In one embodiment, the sensor and the pick-up coil may be inserted in the container using the same port. In other embodiment, the sensor and the pick-up coil may be inserted in the container using separate ports. For example, the sensor may be used in conjunction with disposable bioprocess components to monitor the parameters inside the components during or after the operation. In certain embodiments, the LCR sensor functions by generating a sensor output that relies on a coupling between the LCR sensor and a corresponding pick-up coil.

Now referring to FIG. 1, a sensing system, for example a radio frequency identification (RFID) sensing system 10 in accordance with an exemplary embodiment is disclosed. In the illustrated embodiment, an equivalent sensor circuit of the system 10 is shown. The sensing system 10 includes an LCR sensor 12 with an IC memory chip 14, a pick-up coil (detector) 16. The IC memory chip 14 is used for storing information and may be activated by a radio frequency signal transmitted from a read/write unit 18. The sensor 12 receives and transmits radio frequency signals. The pick-up coil 16 is disposed in operative proximity of the sensor 12 so as to pick up signals transmitted by the sensor 12. In one embodiment, the sensor 12 and the pick-up coil 16 may be coupled via an inductive coupling. In a preferred embodiment, the sensor 12 and the pick-up coil 16 may be adapted to communicate wirelessly. In certain embodiments, an IC memory chip is not required and an LCR sensor 12 can operate without the IC memory chip.

The memory chip 14 is read by the read/write unit 18 by illuminating the sensor 12 tuned by a combination of a sensor inductance (L), a sensor capacitance (C), and a sensor resistance (R). The combination of the inductance, the capacitance, and the resistance is termed an "LCR resonant circuit". When a radio frequency field passes through a sensor coil (not shown in FIG. 1), an AC voltage is generated across the sensor coil. This voltage is rectified in the memory chip 14 to result in a DC voltage for the chip operation. The chip 14 becomes functional when the DC voltage reaches a predetermined level needed to activate and operate the memory chip 14. By detecting the radio frequency signal backscattered from the memory chip 14, the information stored in the memory chip 14 can be identified.

To activate the memory chip 14, the read/write unit 18 sends a radio frequency signal that is captured by the sensor coil of the sensor 12, generating an AC voltage across the sensor coil. An on-chip rectifier (not shown) further converts the AC voltage into a DC voltage that activates the memory chip 14. The activated chip 14 is capable of sending stored information back to the read/write unit 18 and is capable of receiving new information to be stored into the memory. The read/write unit 18 uses command pulses to communicate with the chip 14 for reading and writing data.

For selective analyte quantitation using the LCR sensor 12, impedance spectra of the sensor are measured. "Analyte" refers to the substance or condition being analyzed. In the illustrated embodiment, the sensor circuit of the sensor 12 is represented by impedance ($Z_s$) of an electrode structure, impedance ($Z_{s/f}$) of a sensing film, impedance ($Z_f$) of an interface between the electrode structure and the sensing film, impedance ($Z_{f/a}$) of an interface between the sensing film and an analyzed fluid, impedance ($Z_a$) of the analyzed fluid. In the illustrated embodiment, the impedances are shown in parallel. In certain other embodiments, the impedances may be in series. The sensor 12 is interrogated via the pick-up coil 16 having an impedance ($Z_c$).

Figure 2:
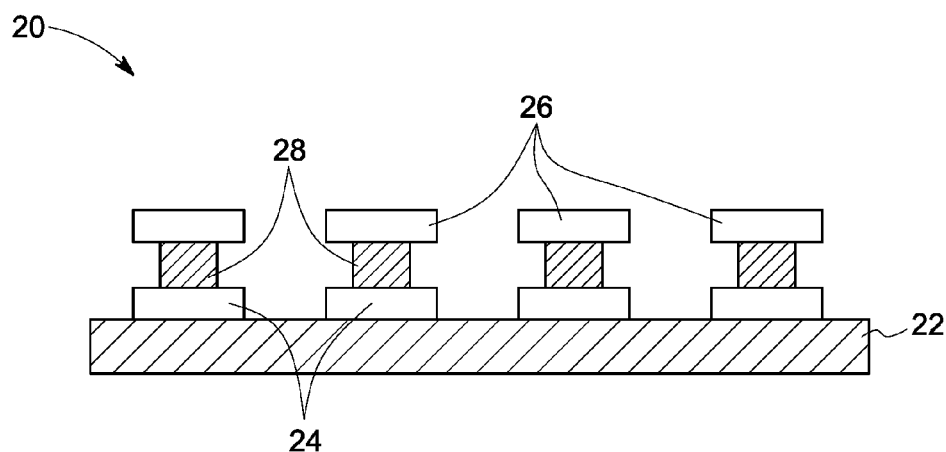
FIG. 2 is a sectional view of an electrode structure of an LCR sensor in accordance with an exemplary embodiment of the present invention.

Referring to FIG. 2, an electrode structure 20 of the LCR sensor in accordance with an exemplary embodiment of the present invention is disclosed. In the illustrated embodiment, the electrode structure 20 includes a substrate 22, a plurality of first sensing elements 24 mutually spaced apart and disposed on the substrate 22. The electrode structure 20 further includes a plurality of second sensing elements 26; each second sensing element 26 is disposed overlapping the corresponding first sensing element 24. An isolator 28 (may also be referred to as a "dielectric layer" or "dielectric isolator") is disposed between the corresponding first and second sensing elements 24, 26. The isolator 28 may be used to prevent electrical shortening and loss of the sensor resonance. In some embodiments, the LCR sensor is a multivariable LCR sensor. In certain embodiments, the first sensing element 24 is non-galvanically coupled to second sensing element 26.

Figure 3:
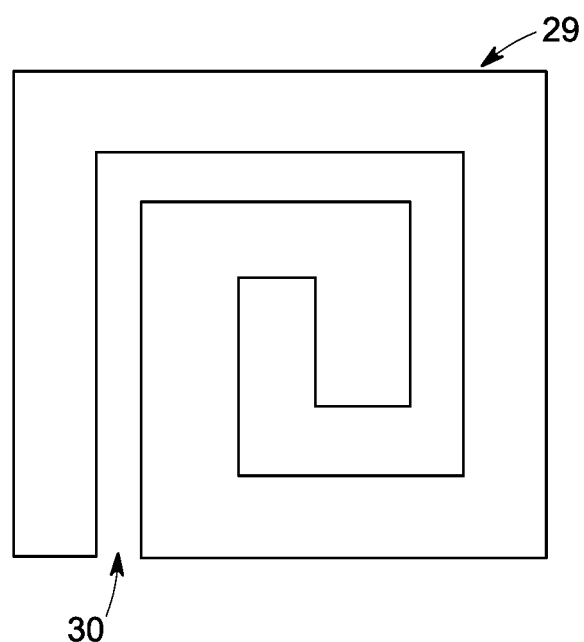
FIG. 3 is a top view of the electrode structure in accordance with an embodiment of FIG. 2.

Referring to FIG. 3, a top view of the electrode structure 20 (shown in FIG. 2) is illustrated. It should be noted herein that the plurality of first and second sensing elements 24, 26 (shown in FIG. 2) together form a sensing coil structure 29. Such a sensing coil structure 29 may be fabricated using techniques not limited to a complementary metal-oxide-semiconductor (CMOS) fabrication process, inkjet printing, screen printing, laser cutting, selective etching, or the like. In some embodiments, groups of such sensing elements 24, 26 form an array of such coil structures 29. It should be noted herein that the number of sensing elements, their orientation, and geometry may be varied depending upon the application. In some embodiments, groups of such sensing elements 24, 26 form an array of structures that are not coils but other types of LCR resonators. Non-limiting examples of such LCR resonators operating at different frequencies are split ring resonators with a single or multiple cuts, dual-split ring resonators, closed rings, slab-pairs, cross-shaped structures, coupled strips, posts, wires, and their combinations.

Fabrication of the sensing elements to form a coil structure 29 with a dielectric gap 30, for example, provides the ability to obtain inductance of the sensing elements. Such an inductance directly contributes to the LCR sensor performance. Also, fabrication of the sensing elements as inter-digital electrodes on top of each other and separated with a dielectric gap provides the ability to obtain large area for interactions with environment around the sensing elements. Furthermore, fabrication of the sensing elements as other types of LCR structures with nonlimiting examples of geometries as described above with one on top of each other and separated with a dielectric gap provides the ability to obtain large area for interactions with environment around the sensing elements.

Figure 4:
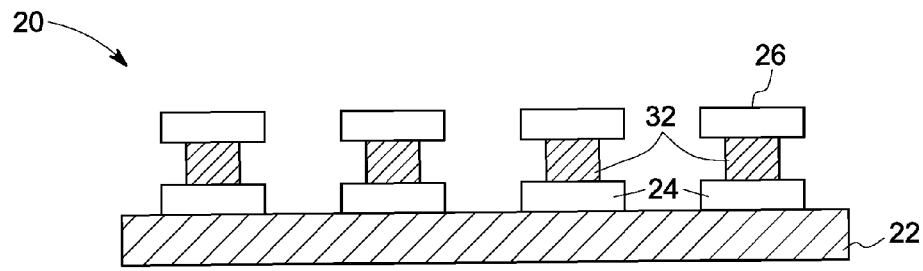
FIG. 4 is a sectional view of an electrode structure in accordance with an exemplary embodiment of the present invention.

Referring to FIG. 4, the electrode structure 20 in accordance with an exemplary embodiment of the present invention is disclosed. In the illustrated embodiment, a dielectric gap material 32 between the first and second sensing elements 24, 26 may serve as a "sensing layer". The height and a dielectric constant of the dielectric gap material 32 may vary depending upon interactions with the analytes. The height of the dielectric gap material 32 may vary due to swelling of the dielectric gap material 32 because of the sorption uptake of an analyte. The dielectric constant of the dielectric gap material 32 may also vary because of the sorption uptake of an analyte.

In one embodiment, the electrode structure 20 may be fabricated by first applying the plurality of first sensing elements 24 to the substrate 22 having a predetermined shape. The dielectric layer 32 is then applied to the plurality of first sensing elements 24. The plurality of second sensing elements 26 is then applied corresponding to the positions of the plurality of first sensing elements 24, where the dielectric layer 32 is disposed separating the plurality of first and second sensing elements 24, 26. The shape of the substrate 22 does not change during the fabrication process. In some embodiments, the at least one dielectric layer 32 has a thickness in a range of one to five thousand nanometers.

In another embodiment, the electrode structure 20 may be fabricated by first applying the plurality of first sensing elements 24 to the substrate 22 having a predetermined shape. The dielectric layer 32 is then applied to the plurality of first sensing elements 24. The plurality of second sensing elements 26 is then applied corresponding to the positions of the plurality of first sensing elements 24, where the dielectric layer 32 is disposed separating the plurality of first and second sensing elements 24, 26. A portion of the dielectric layer 32 is removed to form a horizontal gap between the first and second sensing elements 24, 26. The shape of the substrate 22 does not change during the fabrication process. In some embodiments, the at least one dielectric layer 32 has a thickness in a range of one to five thousand nanometers.

Figure 5:
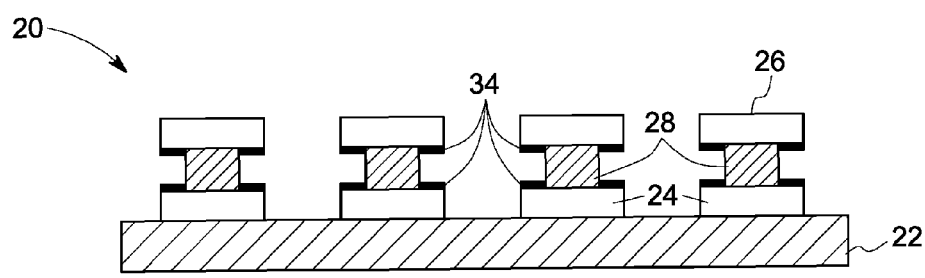
FIG. 5 is a sectional view of an electrode structure in accordance with an exemplary embodiment of the present invention.

Referring to FIG. 5, the electrode structure 20 in accordance with an exemplary embodiment of the present invention is disclosed. In the illustrated embodiment, a gap between the first and second sensing elements 24, 26 may be functionalized by applying a sensing film 34. The same sensing film 34 may be provided to both the first and second sensing elements 24, 26.

The sensing film 34 performs the function of predictably and reproducibly affecting the sensor response upon interaction with a sample. The sensing film material may include a polymeric, organic, inorganic, biological, composite, or a nano composite film that changes property depending on the environment that material is placed in. Additional examples of sensing materials include ionic liquids with organic and inorganic ions, semiconducting nanocrystals, nanotubes, and nano fibers. Additional examples of sensing materials can be in the form of organic molecules, biological molecules, and inorganic molecules. The sensing material can be also in the form of biological organisms such as cells, bacteria, and others known in the art to respond to the environmental changes of the environment.

Examples of properties of a sensing material that are predictably changing upon exposure to the environment include, but are not limited to, changes in capacitance, changes in resistance, changes in thickness, changes in viscoelasticity, or a combination thereof.

Figure 6:
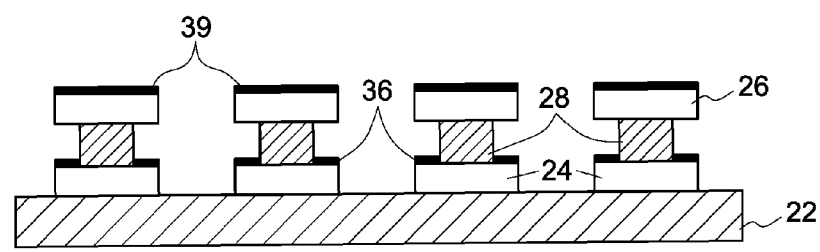
FIG. 6 is a sectional view of an electrode structure in accordance with an exemplary embodiment of the present invention.

Referring to FIG. 6, the electrode structure 20 in accordance with an exemplary embodiment of the present invention is disclosed. In the illustrated embodiment, the first and second sensing elements 24, 26 may be functionalized by applying different sensing films 36, 39 to the first and second sensing elements 24, 26. In particular, each sensing film among the one set of sensing films 26, is disposed on a first sensing region 37 of the corresponding first sensing element 24. Each sensing film among the other set of sensing films 39, is disposed on a second sensing region 39 of the corresponding second sensing element 26. The isolator 28 is disposed between the corresponding first and second sensing elements 24, 26.

In the LCR sensor, sensing response is provided from analyte-dependent change in circuit capacitance, analyte-dependent change in circuit resistance, analyte-dependent change in circuit inductance, or a combination of the three. The combination of changes in the inductance, capacitance and resistance is measured by measuring frequency response spectrum of the LCR resonant sensing circuit. The sensing films 36, 39 are selected for the proper chemical or biological recognition based on the analyte and sensing material properties. The analyte-induced changes in the sensing films 26, 32 affect the impedance of the sensor circuit through the changes in circuit resistance, circuit inductance, and circuit capacitance.

The gap between the sensing elements 24, 26 is controlled by the fabrication process and the intended application of the resulting resonant sensor. The gap between the sensing elements ranging from about 1 nanometer to about 1000 nanometers provides the ability for detection of biological molecules and structures with non-limiting examples that include nucleic acids, proteins, and viruses. The gap between sensing elements ranging from about 1 micrometer to about 1000 micrometers provides the ability for detection of biological molecules and structures with non-limiting examples that include nucleic acids, proteins, viruses, spores, bacteria.

The gap between sensing elements ranging from about 1 nanometer to about 1000 micrometers provides the ability to detect different gaseous analytes when at least one sensing film is positioned within the gap. The gap between sensing elements ranging from about 1 nanometer to about 100 millimeters provides the ability to detect at least one fluid when the fluid is positioned within the gap. The cross-sectional shapes of the sensing elements and the respective gaps between the sensing elements are governed by the intended application of the resonant sensor and the spectral range of performance of the resonant sensor. The cross-sectional shapes of the sensing elements and the respective gaps between the sensing elements can be symmetrical or non-symmetrical, as guided by the design rules of the respective LCR resonators for different frequency ranges.

Figure 7:
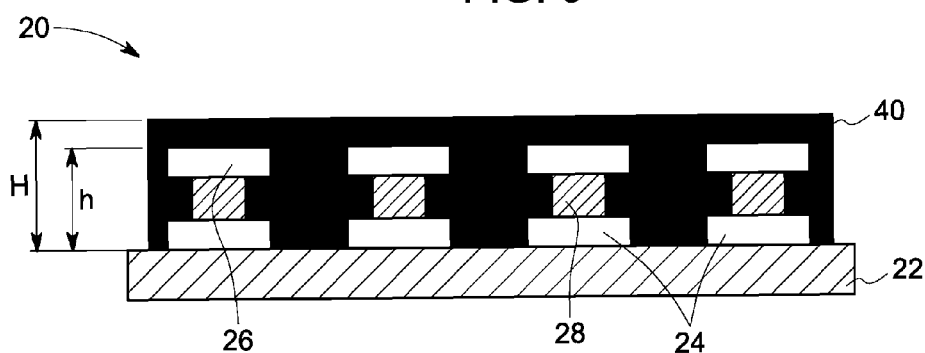
FIG. 7 is a sectional view of an electrode structure in accordance with an exemplary embodiment of the present invention.

Referring to FIG. 7, the electrode structure 20 in accordance with an exemplary embodiment of the present invention is disclosed. In the illustrated embodiment, the first and second sensing elements 24, 26 are substantially covered with a same sensing film 40 which is a protective film. The terms "sensing film" and "protecting film" may be used interchangeably and represented by the numeral 40. The protecting film 40 may be made of materials including at least one of a dielectric material, silicon dioxide, silicon nitride, silicon carbide, parylene, silicone, fluorinated polymers, ceramics, or a combination thereof.

The protecting film 40 is applied onto the first sensing elements 24, the second sensing elements 26, and the dielectric isolators 28. In one embodiment, the protecting film 40 is non-conformally applied onto the first sensing elements 24 and the second sensing elements 26. In the illustrated embodiment, the protecting film 40 is non-conformally applied onto the first sensing elements 24, the second sensing elements 26, and the dielectric isolators 28. In certain other embodiments a protecting film may be conformally applied onto the first sensing elements 24, the second sensing elements 26, and the dielectric isolators 28. An embodiment of the conformal application of a protecting film is shown with reference to FIG. 26 below.

The protecting film 40 which is provided onto the first sensing elements 24, the second sensing elements 26, the substrate 22, and the dielectric isolators 28 is in a physical contact with the analyte. Additionally, the protecting film 40 prevents a direct physical contact of the first sensing elements 24, the second sensing elements 26, and the dielectric isolators 28 with the analyte. As a result, the protecting film 40 prevents the first sensing elements 24, the second sensing elements 26, and the dielectric isolators 28 from damage, degradation, corrosion, and the like.

Furthermore, the protecting film 40 is configured to enable an operational contact of at least one of the first sensing elements 24, the second sensing elements 26, the substrate 22, and the dielectric isolators 28 with the analyte. As used herein, the term "operational contact" refers to a contact that allows interaction of an electromagnetic field generated between the sensing elements 24, 26, and the analyte. The protecting film 40 allows transmission of electromagnetic field generated between the first sensing elements 24 and the second sensing elements 26 to penetrate into the analyte. After penetration and transmission through the protecting film 40, the electromagnetic field interacts with the analyte. Furthermore, the protecting film 40 is configured to be inert to the analyte. In other words, the protecting film 40 is non-responsive to a change in the analyte.

The protecting film 40 has a uniform height H. The total height H of the protecting film 40 is greater than a sum h of a height of the first sensing element 24, a height of the corresponding second element 26 that overlaps the first sensing element 24, and a height of the corresponding dielectric isolator 28 being disposed between the first sensing element 24 and the corresponding second sensing element 26.

In accordance with the embodiments discussed herein, fabrication of gaps between sensing elements include a 3-D micro-gap, nano-gap resonant sensors for physical, chemical, and biological sensing. These 3-D micro-gaps, and nano-gaps are the working gaps responsible for the sensor response. These gaps are formed parallel to the substrate 22 of the sensor during the fabrication of the sensor. These gaps are formed parallel to the substrate 22 of the sensor during the fabrication of the sensor without a step of folding the substrate when a gap between the sensing elements is formed after substrate folding.

The 3-D micro-gap or nano-gap in the resonant sensor facilitates high sensitivity measurements, and also enables wired or wireless readout. The 3-D micro-gap or nano-gap is related to the operational frequency of the antenna of the resonant sensor where the operational frequency range from hundreds of kHz to MHz, GHz, THz, IR, near-IR, visible, and UV spectral ranges.

In conventional resonant sensors, a sensing gap is formed vertically between the sensing elements. In accordance with embodiments of the present invention employing a 3-D approach, gap is formed horizontally between the sensing elements. Such an exemplary approach provides the ability for a controlled formation of nano-gaps with high aspect ratio. Further, the horizontal gap between the sensing elements provides a relatively larger sensing volume as compared to the vertical gap in conventional resonant sensors because of the limitation of the maximum height of sensing elements that can be fabricated with the vertical gaps.

Figure 8:
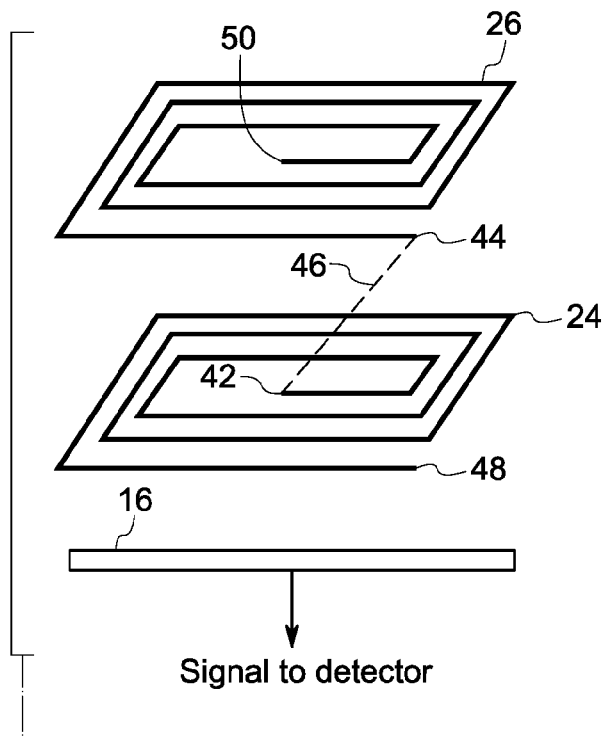
FIG. 8 is a diagrammatical representation of a first sensing element and the second sensing element of an electrode structure in accordance with an exemplary embodiment of the present invention.

Referring to FIG. 8, a diagrammatical representation of the first sensing element 24 and the second sensing element 26 is shown in accordance with an exemplary embodiment of the present invention. The second sensing element 26 is spaced apart and disposed overlapping the first sensing element 24. The first and second sensing elements 24, 26 are disposed proximate to the pick-up coil 16.

In the illustrated embodiment, a first end 42 of the first sensing element 24 is coupled to one end 44 of the second sensing element 26 via a connector 46. In another embodiment, a second end 48 of the first sensing element 24 is coupled to another end 50 of the second sensing element 26. In yet another embodiment, the first end 42 of the first sensing element 24 is coupled to the other end 50 of the second sensing element 30. In yet another embodiment, the second end 48 of the first sensing element 24 is coupled to one end 44 of the second sensing element 26. In the illustrated embodiment, the first and second sensing elements 24, 26 are wireless sensing elements. The term "wireless" indicates that there is no electrical (galvanic) contact between the resonant sensor and the sensor reader. Instead, the connection between the resonant sensor and the sensor reader is performed either through inductive coupling, capacitive coupling, or optical coupling.

Figure 9:
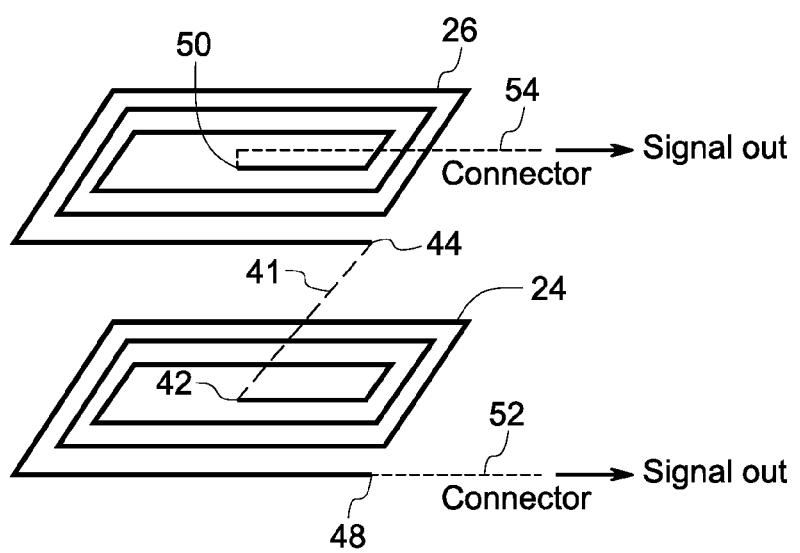
FIG. 9 is a diagrammatical representation of a first sensing element and the second sensing element of an electrode structure in accordance with an exemplary embodiment of the present invention.

Referring to FIG. 9, a diagrammatical representation of the first sensing element 24 and the second sensing element 26 is shown in accordance with an exemplary embodiment of the present invention. The second sensing element 26 is spaced apart and disposed overlapping the first sensing element 24. In the illustrated embodiment, the first and second sensing elements 24, 30 have connectors 52, 54 respectively for transmitting sensor outputs. In other words, the first and second sensing elements 24, 26 are wired sensing elements.

Figure 10:
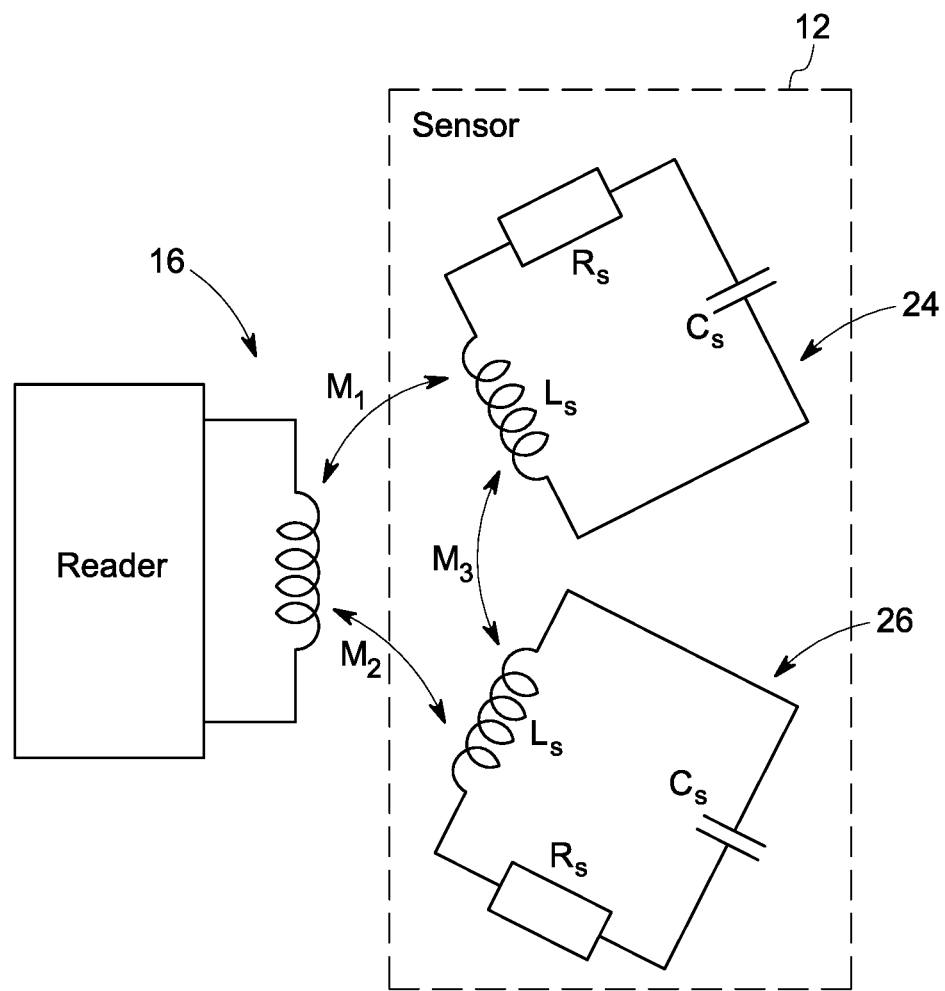
FIG. 10 is a diagrammatical representation of an LCR sensor disposed in proximity to the pick-up coil in accordance with an exemplary embodiment of the present invention.

Referring to FIG. 10, a diagrammatical representation of the LCR sensor 12 disposed in proximity to the pick-up coil 16 is disclosed. The sensor 12 has two sensing elements 24, 26 that are inductively coupled with each other and are inductively coupled to the pick-up coil 16. Inductance between the first sensing element 24 and the pick-up coil 16 is represented by "$M_1$", inductance between the second sensing element 26 and the pick-up coil 16 is represented by "$M_2$", and inductance between the first and second sensing elements 24, 26 is represented by "$M_3$". Each of the sensing elements is tuned by a combination of a sensor inductance (L), a sensor capacitance (C), and a sensor resistance (R).

It should be noted herein that the feature of using at least two sensing elements 24, 26 in the resonant sensor is to introduce an orthogonal response which is the number of orthogonal axes after the multivariate analysis that contains the analyte-relevant information and correlates with the amount of detected analyte.

An individual LCR sensor typically produces a capacitive and resistive response. A change in the position between the pickup coil and the sensor also affects the inductance response but this inductance response is unrelated to analyte concentration but rather related to the pick-up coil positioning. In accordance with the embodiments of the present invention, the fabrication of a resonant sensor with two or more sensing elements on a single substrate provides the ability to modulate inductance of the resulting sensor. The inductance is modulated when sensing elements change their position relative to each other as a function of analyte type and concentration. In one embodiment, change in position of the sensing elements is induced by swelling of the micro-gap or nano-gap (see FIG. 4). In another embodiment, the change in position of the sensing elements is induced by swelling of the sensing film (see FIG. 4) that changes the geometry of the sensing elements.

Figure 11:
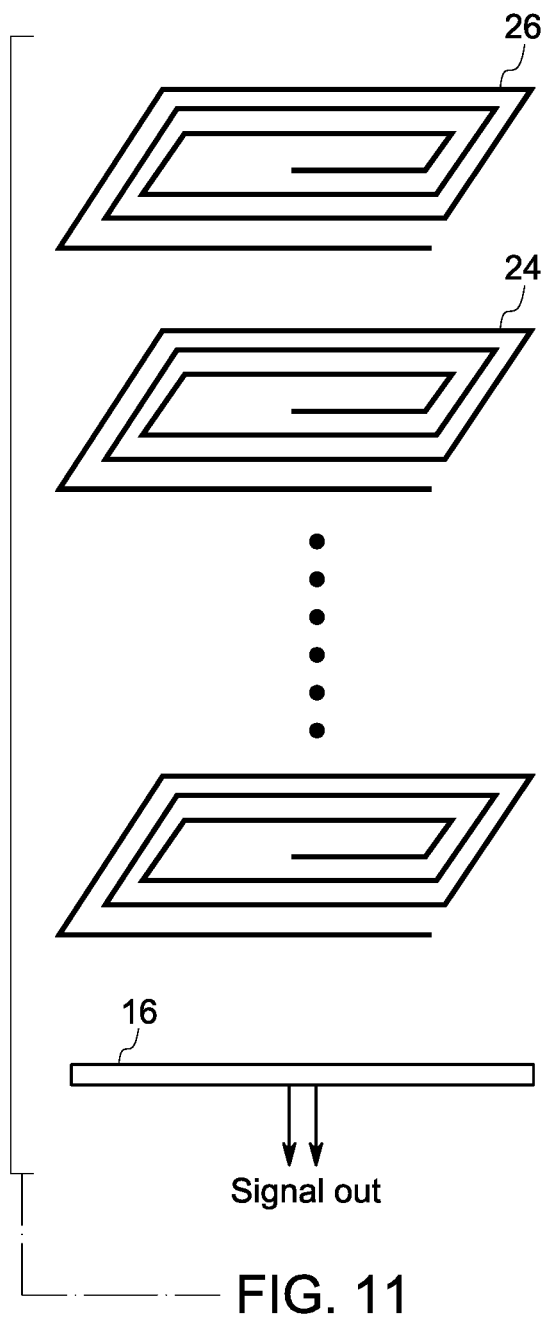
FIG. 11 is a diagrammatical representation of a plurality of sensing elements in accordance with an exemplary embodiment of the present invention.

Referring to FIG. 11, a diagrammatical representation of a plurality of sensing elements is shown in accordance with an embodiment of the present invention. The plurality of sensing elements are spaced apart and disposed overlapping each other. A sensor signal is received wirelessly using the pick-up coil 16.

The LCR resonant sensor may be operated in the radio-frequency range, microwave range, and optical range depending on the operation frequency range of the sensor. In these operation ranges, wireless excitation of the LCR resonant sensor and signal collection from the LCR resonant sensor may be performed using different methods. In one embodiment, for a radio-frequency range operation of the sensor, non-limiting examples include wireless excitation and signal collection via a pick-up coil. In another embodiment, for a microwave range operation of the sensor, non-limiting examples include wireless excitation and signal collection via a monopole antenna and a horn antenna. In yet another embodiment, for an optical range operation of the sensor, non-limiting examples include wireless excitation and signal collection via a halogen lamp and a spectrometer.

Figure 12:
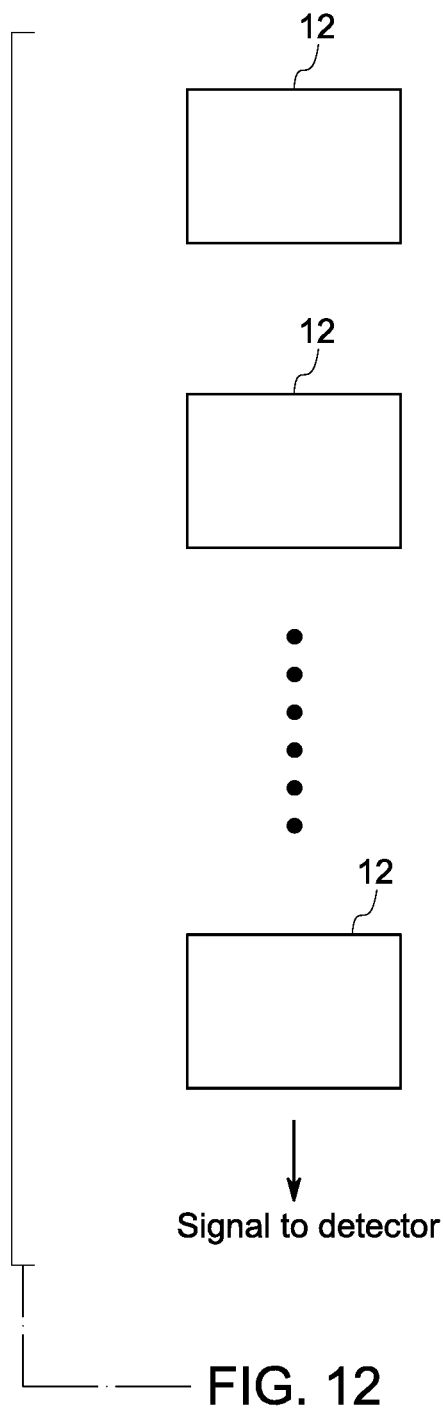
FIG. 12 is a diagrammatical representation of a plurality of LCR sensors in accordance with an exemplary embodiment of the present invention.

Referring to FIG. 12, a diagrammatical representation of a plurality of LCR sensors 12 are shown in accordance with an embodiment of the present invention. In one embodiment, "n" number of LCR sensors 12 are disposed proximate to the pick-up coil. In certain embodiments, "n" number of corresponding pick-up coils may be used. The number of pick-up coils and LCR sensors 12 may vary depending on the application. The sensor excitation response may be detected and analyzed via a network analyzer or other measurement system. In some embodiments, instead of a pick-up coil, other techniques may be used for receiving signals based on frequency range of measurements.

Figure 13:
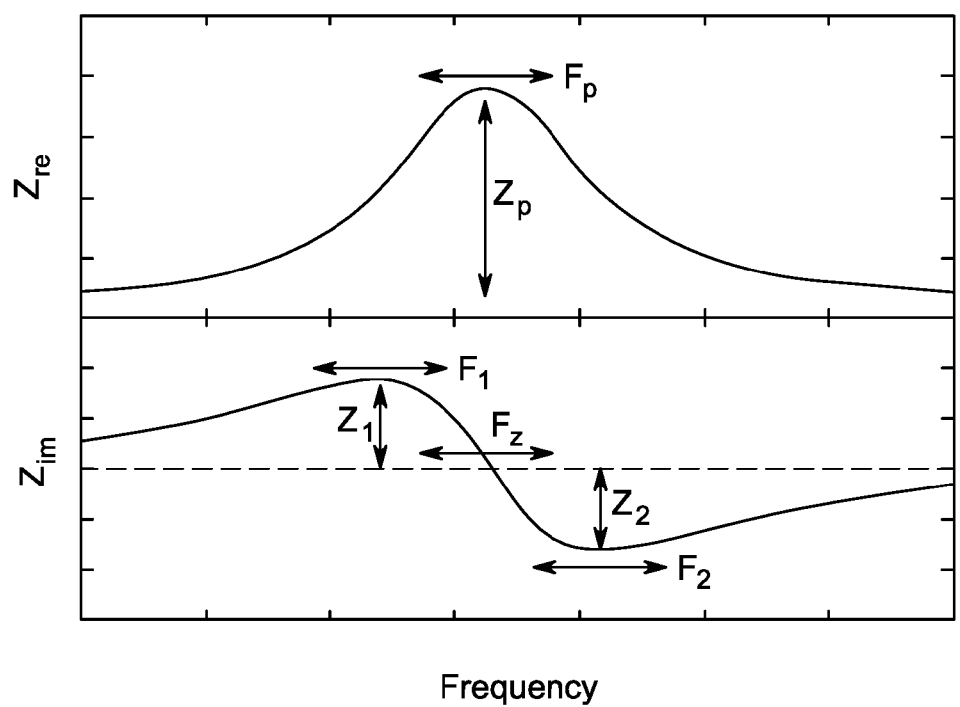
FIG. 13 is graphical representation of an impedance spectrum of an LCR sensor used for measuring one or more properties of an analyte, in accordance with an exemplary embodiment of the present invention.

Referring to FIG. 13, an impedance spectrum of the LCR sensor for measuring one or more properties of an analyte is illustrated in accordance with an embodiment of the present invention. X-axis is represented by "frequency" of the spectrum and Y-axis is represented by "impedance" (Z) of the spectrum. The spectrum includes a real part ($Z_{re}$) of the impedance spectrum, an imaginary part ($Z_{im}$) of the impedance spectrum, frequency of the maximum of the real part of the impedance ($F_p$), peak magnitude of the real part of the impedance ($Z_p$), peak frequency ($F_1$) and magnitude ($Z_1$) of the imaginary part of the impedance, resonant frequency ($F_2$) and magnitude ($Z_2$) of the imaginary part of the impedance, and frequency ($F_z$) at which the imaginary portion of impedance is zero.

Additional parameters that can be extracted from a response of the LCR sensor circuit may include quality factor of resonance, phase angle, or the like. Use of multivariate analysis reduces the dimensionality of the multivariable LCR sensor response to a single data point in multidimensional space for selective quantitation of different parameters of an analyte. Examples of multivariate analysis include canonical correlation analysis, regression analysis, nonlinear regression analysis, principal components analysis, discriminate function analysis, multidimensional scaling, linear discriminate analysis, logistic regression, and/or neural network analysis. Quantitation of analytes is performed using the exemplary LCR sensor by applying multivariate analysis of the full impedance spectrum. In certain embodiments, other spectral parameters, related to the impedance spectrum such as S-parameters (scattering parameters) and Y-parameters (admittance parameters) may be measured.

Figure 14:
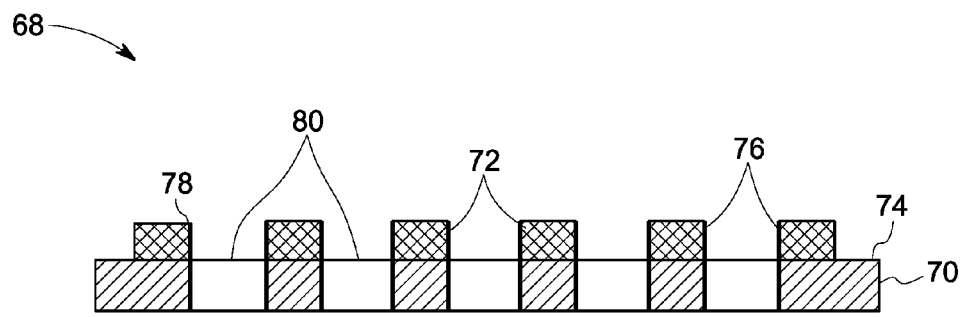
FIG. 14 is a sectional view of an electrode structure of an LCR sensor in accordance with an exemplary embodiment of the present invention.

Referring to FIG. 14, an electrode structure 68 of an LCR sensor in accordance with an exemplary embodiment of the present invention is disclosed. In the illustrated embodiment, the electrode structure 68 includes a substrate 70, a plurality of first sensing elements 72 mutually spaced apart and disposed on a first surface 74 of the substrate 70, one set of sensing films 76, each sensing film among the one set of sensing films 76, being disposed on a first sensing region 78 of the corresponding first sensing element 72. In the illustrated embodiment, the first sensing region 78 is a vertical region of the first sensing element 72. The substrate 70 further includes a plurality of holes 80 formed in the substrate 70; the holes 80 being disposed between the plurality of first sensing elements 72. The holes 80 facilitate flow of the sample medium through the substrate 70. Non-limiting examples of positioning of sensing films 76 include vertical regions of the first sensing elements 72 and/or on the vertical regions on holes 80 in the substrate 70.

The electrode structure 68 in accordance with this embodiment provides the ability for measurements of biological samples in a flow-through configuration that significantly reduces the time needed to achieve sensor response because of the mass-transport limitation.

In the illustrated embodiment, an electrical field distribution between the sensing elements 72 is substantially uniform in the plane of electrode structure 68 i.e. the electric field distribution between the plurality of first sensing elements 72 is substantially uniform along a plane of the plurality of first sensing elements 72 and the holes 80. Having the sensing holes 80 between the sensing elements 72 for the flow-through of biological molecules and particles (such as viruses, bacteria, spores, etc.) provides the advantage of reliable detection of these biological moieties in any region of the sensing holes 80. In some embodiments, the sensing holes 80 may further include nano-holes or micro-holes for the flow-through of the sample. In certain embodiments, the interior of the sensing holes 80 may be functionalized by a receptor film layer to provide selective detection. The plurality of nano-holes or micro-holes in the sensing holes may be also functionalized using a receptor film layer to provide selective detection. The plurality of nano-holes or micro-holes in the sensing holes 80 increases the surface area for interaction of the receptor film layer with an analyte passing through the sensing holes. The flow-through configuration of the illustrated embodiment, enables reductions in assay time and sample volumes, enhancing the utility of sensors.

Figure 15:
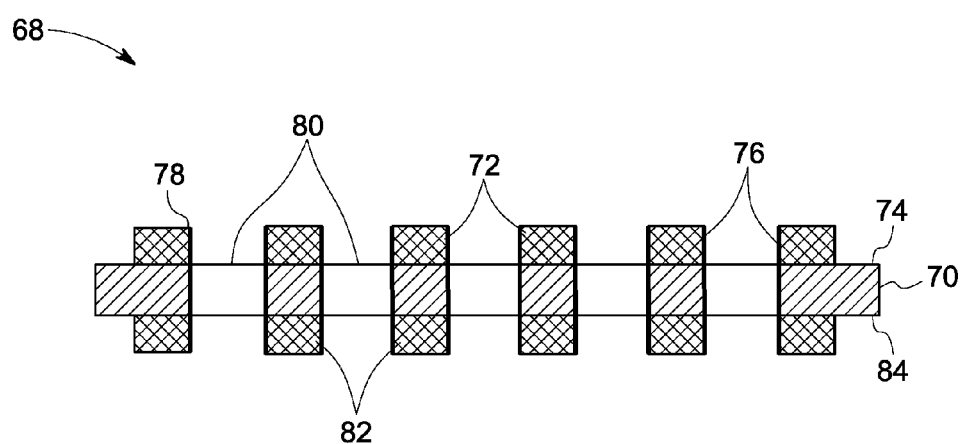
FIG. 15 is a sectional view of an electrode structure of an LCR sensor in accordance with an exemplary embodiment of the present invention.

Referring to FIG. 15, an electrode structure 68 of an LCR sensor in accordance with an exemplary embodiment of the present invention is disclosed. The electrode structure 68 is similar to the embodiment of FIG. 14. Additionally, the electrode structure 68 further includes a plurality of second sensing elements 82 disposed on a second surface 84 opposite to the first surface 74 of the substrate 70. The plurality of holes 80 in the substrate 70; are disposed between the plurality of first and second sensing elements 72, 82. A set of sensing films 76, each sensing film among the set of sensing films 76, being disposed on a first sensing region 78 of the corresponding first sensing element 72. Nonlimiting examples of positioning of sensing films 76 include the vertical regions of the sensing elements 72, 82 and/or on the vertical regions on holes 80 in the substrate 70.

In one embodiment, sensing elements on one side of the sensor substrate 70 serve as "sensing electrodes", while sensing elements on the other side of the sensor substrate 70 serve as "reference electrodes". The use of sensing and reference electrodes provides the ability for correction for environmental instabilities such as temperature effects, or the like. Such a correction is performed when temperature affects both sensing and reference electrodes while the analyte concentration change affects only the sensing electrodes.

In another embodiment, sensing electrodes on one side of the substrate 70 operate at one resonance frequency, while sensing electrodes on the other side of the sensor substrate 70 operate at another resonance frequency. Operation of the sensing electrodes at at least two frequencies provides the ability for more selective measurements, where sensing effects at different frequencies originate from diverse interactions of the sensing film and an analyte.

Figure 16:
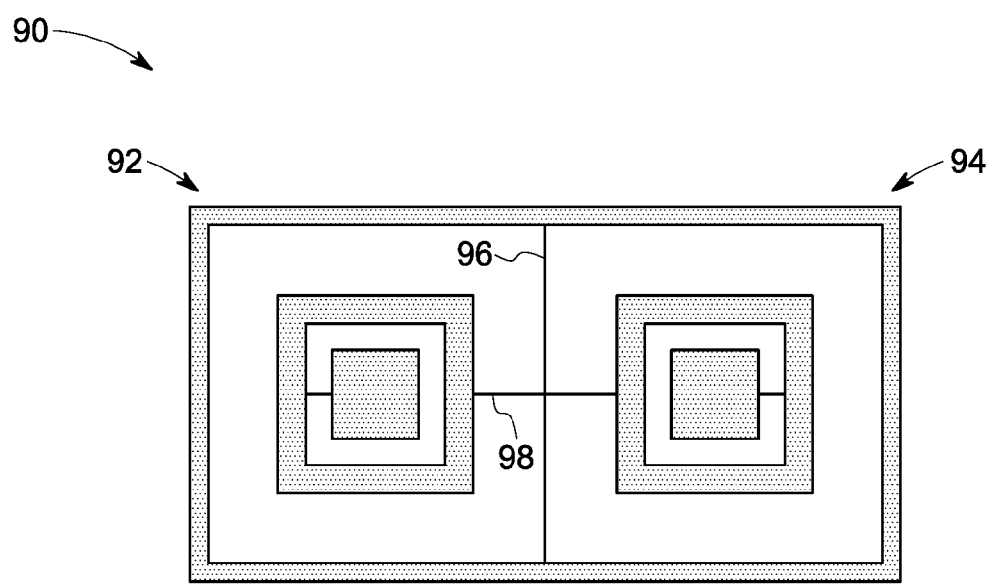
FIG. 16 is a diagrammatical representation of a split ring resonator (SRR) sensor in accordance with an exemplary embodiment of the present invention.

Referring to FIG. 16, an exemplary sensor 90 in accordance with an exemplary embodiment of the present invention is disclosed. In the illustrated embodiment, compared to FIG. 2, the sensor 90 is a split ring resonator (SRR) sensor, in particular, a dual split ring resonant sensor. The sensor 90 includes concentric split rings 92, 94 with sensing regions 96, 98. In the illustrated embodiment, the sensing regions 96, 98 are devoid of any patterns.

The electric field distribution in the sensing element is spread along the length of the sensing region. The electric field distribution in the split ring resonator structure is spread along the length of the sensing regions 96 and 98.

Figure 17:
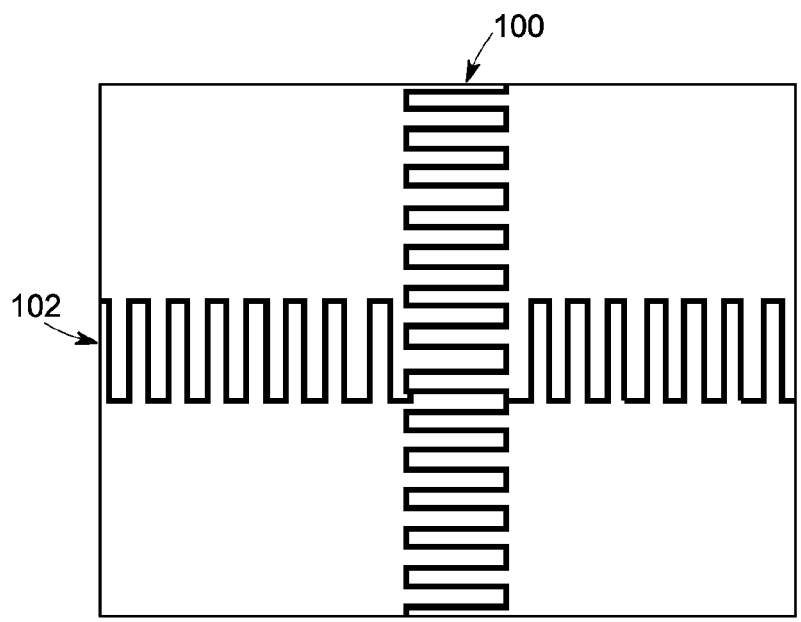
FIG. 17 is a diagrammatical representation of a split ring resonator (SRR) sensor in accordance with an exemplary embodiment of the present invention.

Referring to FIG. 17, a split ring resonant sensor in accordance with an exemplary embodiment of the present invention is disclosed. In the illustrated embodiment, the split ring resonant sensor includes sensing regions 100, 102 having meander (serpentine) shaped patterns.

Figure 18:
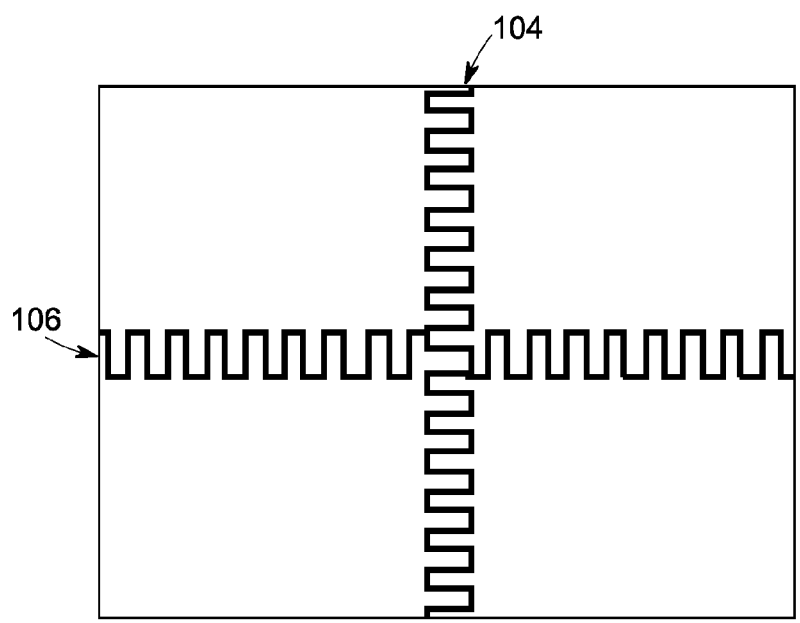
FIG. 18 is a diagrammatical representation of a split ring resonator (SRR) sensor in accordance with an exemplary embodiment of the present invention.

Referring to FIG. 18, a split ring resonant sensor in accordance with an exemplary embodiment of the present invention is disclosed. In the illustrated embodiment, the split ring resonant sensor includes sensing regions 104, 106 having meander shaped patterns. It should be noted herein that sensing regions 104, 106 having smaller cross-sectional area compared to sensing regions 100, 102 shown in FIG. 17.

Figure 19:
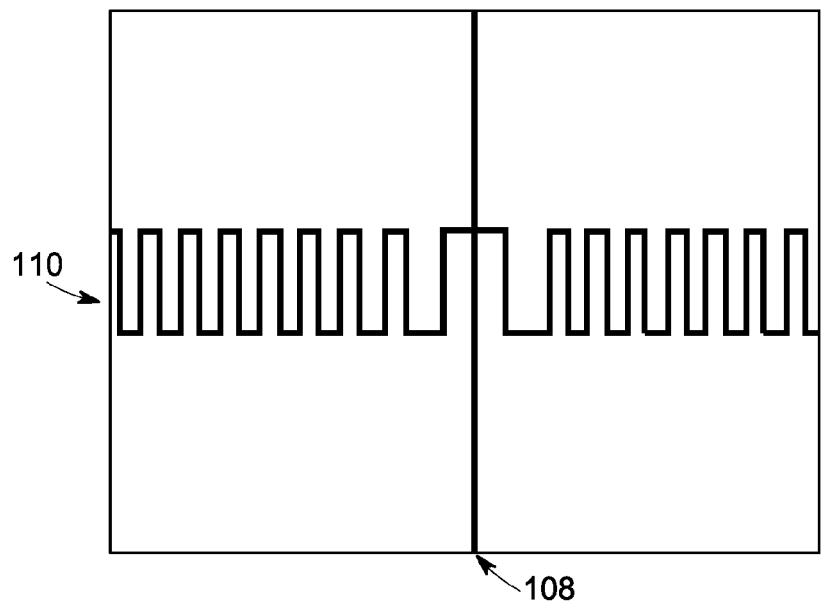
FIG. 19 is a diagrammatical representation of a split ring resonator (SRR) sensor in accordance with an exemplary embodiment of the present invention.

Referring to FIG. 19, a split ring resonant sensor in accordance with an exemplary embodiment of the present invention is disclosed. In the illustrated embodiment, the split ring resonant sensor includes sensing regions 108, 110. The sensing region 108 is devoid of patterns and the sensing region 110 has a meander shaped pattern.

Figure 20:
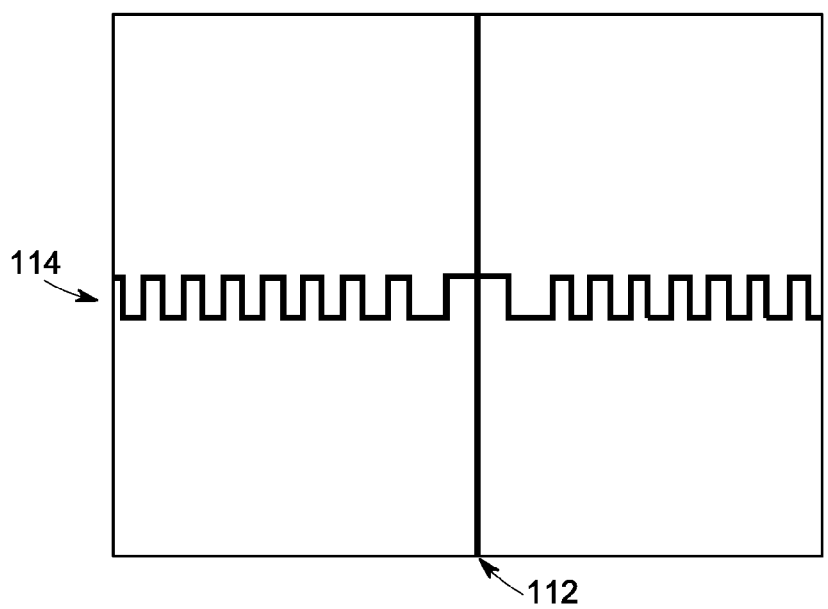
FIG. 20 is a diagrammatical representation of a split ring resonator (SRR) sensor in accordance with an exemplary embodiment of the present invention.

Referring to FIG. 20, a split ring resonant sensor in accordance with an exemplary embodiment of the present invention is disclosed. In the illustrated embodiment, the split ring resonant sensor includes sensing regions 112, 114. The sensing region 112 is devoid of patterns and the sensing region 114 has a meander shaped pattern having relatively smaller cross-sectional area.

The sensing regions of split ring resonant sensors may have different geometries with non-limiting examples of the sensing regions of resonators as shown in FIG. 16-20. The non-limiting examples of geometries of the sensing region may include straight, interdigital fingers, circular, semi-circular, or the like. The geometries provide different gap sizes, total surface area of the gap, and the ratio of the gaps in different directions. Such geometries enhance the active sensing area of the resonant sensor. It should be noted herein that the depth of field penetration is tuned by the controlled geometry.

Referring to FIG. 21, a dual-SRR (split ring resonator) sensor 116 in accordance with an exemplary embodiment of the present invention is illustrated. The SRR sensor 116 includes two pairs of sensing elements 118, 120 disposed on a dielectric substrate 122. The sensing elements 118, 120 may be fabricated by selective etching, printing, lithography, or the like. One pair of sensing elements 118 includes two concentric C-shaped conductive bands 124, 126 and the other pair of sensing elements 120 includes two concentric C-shaped conductive elements 128, 130. It should be noted herein that in each pair of sensing elements, the two concentric C-shaped conductive elements are separated from each other by a gap. The pair of sensing elements 118, 120 are separated from each other by a gap 132. The inner conductive bands 126, 130 are oriented 180 degree relative to each other. The shape of the concentric conductive bands 124, 126, 128, 130 may be rectangular, circular, diamond, hexagon, octagon, or any other shape. The pair of sensing elements 118, 120 includes openings 134, 136 respectively.

The pair of sensing elements 118, 120 are disposed facing each other. Each pair of sensing elements has a self-resonance inductance L due to the finite length of its ring structure. The dual SRR sensor 116 has a plurality of capacitive coupling areas, namely, individual gap of each conductive band, the gap between two outer conductive bands 124, 128, the gap between inner and outer conductive bands. Since each conductive band has a self-inductance and aforementioned capacitive gaps, dual-SRR operates as L-C-R (inductance-capacitance-resistance) resonating structure.

Referring to FIG. 22, the dual-SRR sensor 116 is represented as an L-C-R equivalent circuit in accordance with the embodiment of FIG. 21. The outer conductive band 124 is represented as a series R1-L1-C1, which is coupled to the inner conductive band 126 both inductively and capacitively. The inner conductive band 126 is represented as a series R3-L3-C3. The capacitive coupling between the conductive bands 124, 126 is represented as a parallel circuit R13-C13. R13 is representative of a stray resistance of the resonant sensor.

Similarly, the outer conductive band 128 is represented as a series R2-L2-C2, which is coupled to the inner conductive band 130 both inductively and capacitively. The inner conductive band 130 is represented as a series R4-L4-C4. The capacitive coupling between the conductive bands 128, 130 is represented as a parallel circuit R24-C24. Capacitive coupling between the outer conductive bands 124, 128 is represented as a parallel circuit R12-C12. It should be noted herein M1 represents inductive coupling between outer conductive bands 124, 128, M2 represents inductive coupling between conductive bands 124, 126, and M3 represents inductive coupling between conductive bands 128, 130.

The dual-SRR sensor is excited electromagnetically to create both electric and magnetic resonances. The magnetic field is perpendicular to the SRR plane, while the electric field is excited parallel to a slit of the sensor. It should be noted herein that the area of the sensor excited by the magnetic resonance is relatively smaller than the area of the sensor excited by the electric resonance case. The electric and magnetic resonances can be excited in different sensing regions of the SRR sensor. The SRR sensor may be excited in either by magnetic resonance only or by electric resonance by controlling physical geometries (slits, gaps, and distance between inner and outer conductive bands).

In one embodiment, one side of SRR sensor may be provided with a dielectric sensing film beneath, for levitating the one side of SRR sensor by swelling the sensing film. As a result, electric resonant frequency is influenced more than the magnetic resonance. In another embodiment, magnetic resonance may be separately controlled. For example, magnetic resonance may be controlled by controlling mutual inductances M2, M3. In a specific embodiment, for example, the pair of sensing elements 120 may be provided with a dielectric sensing film underneath the elements 120 for levitating one side of the sensor by swelling the sensing film so as to obtain different mutual inductances M2, M3. These different mutual inductances induce different magnetic field strength, thereby affecting the magnetic resonance more than the electric resonance.

Figure 23:
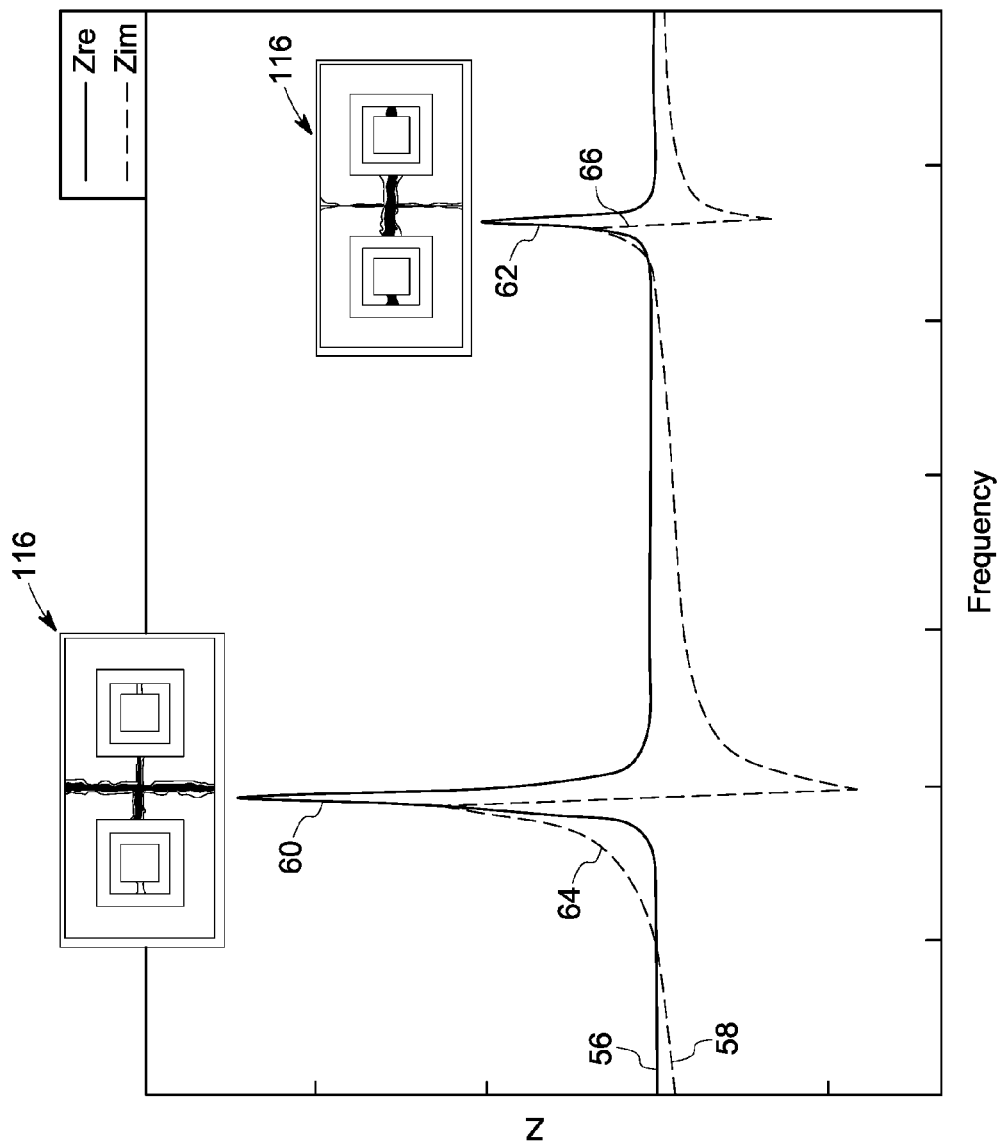
FIG. 23 is a graphical representation of a resonance impedance spectrum of an LCR sensor for measuring one or more properties of an analyte in accordance with an exemplary embodiment of the present invention.

Referring to FIG. 23, a resonance impedance spectrum of the LCR sensor for measuring one or more properties of an analyte is illustrated in accordance with an embodiment of the present invention. X-axis is represented by "frequency" of the spectrum and Y-axis is represented by "impedance" (Z) of the spectrum. The illustrated embodiment shows a curve 56 indicative of a real part ($Z_{re}$) of the impedance spectrum superimposed with a curve 58 indicative of an imaginary part ($Z_{im}$) of the impedance spectrum. In one embodiment, when the magnetic field is perpendicular to the plane of the split ring resonant sensor 116, while electric field is excited parallel to a slit of a split ring of the sensor 116, peak 60 may be representative of an electrical component of the real part of the impedance spectrum, and peak 62 may be representative of a magnetic component of the real part of the impedance spectrum. In another embodiment, when the magnetic field is perpendicular to the plane of the split ring resonant sensor, while the electric field is excited parallel to the gap of the split ring, peak 60 may be representative of a magnetic component of the real part of the impedance spectrum, and peak 62 may be representative of an electrical component of the real part of the impedance spectrum. Similarly, in one embodiment, peak 64 may be representative of an electrical component of the imaginary part of the impedance spectrum, and peak 66 may be representative of a magnetic component of the imaginary part of the impedance spectrum. In another embodiment, peak 64 may be representative of a magnetic component of the imaginary part of the impedance spectrum, and peak 66 may be representative of an electrical component of the imaginary part of the impedance spectrum.

The measurement of two resonances such as magnetic and electrical components provides the ability to increase the sensor response selectivity. The increase in sensor selectivity is due to the different effects of the environment on the magnetic and electrical components of the resonance spectra. In particular, the electrical component of the resonance spectrum preferentially responds to the change in the complex permittivity of the environment. The real part of the complex permittivity of the fluid is referred to as a "dielectric constant". The imaginary part of the complex permittivity of the fluid is referred to as a "dielectric loss factor". The imaginary part of the complex permittivity of the fluid is directly proportional to conductivity of fluid. The magnetic component of the resonance spectrum preferentially responds to the change in the spacing between sensing elements in the sensor structure due to swelling or shrinking of sensing films on the sensing elements.

Figure 24:
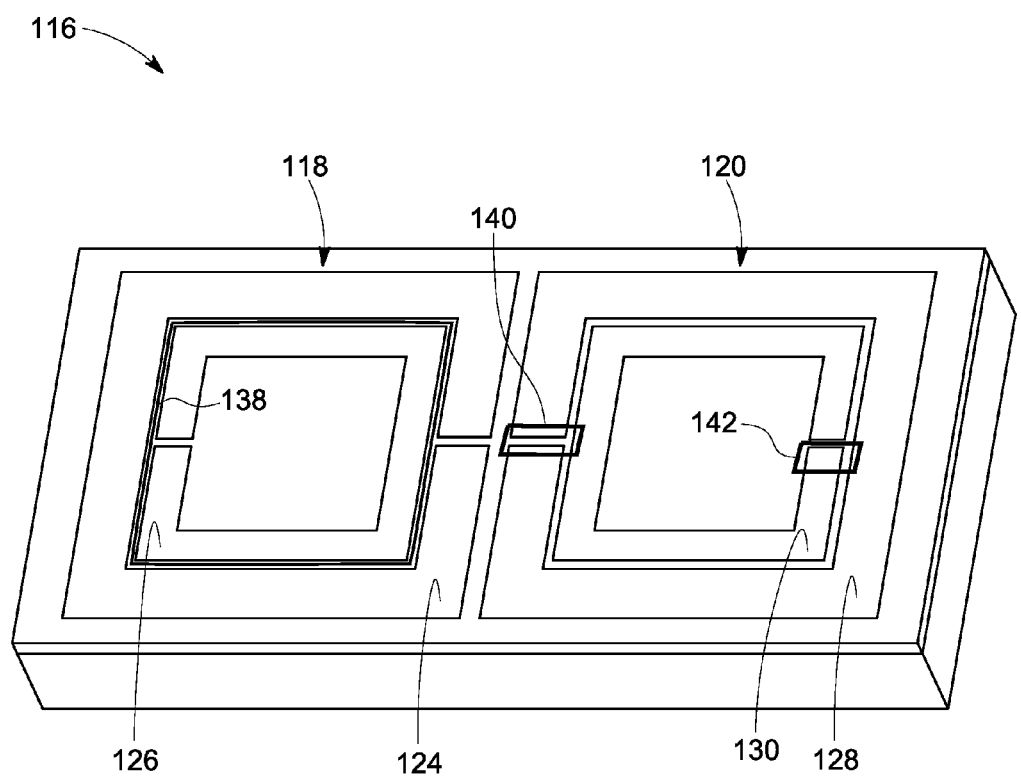
FIG. 24 is a perspective view of a dual-SRR sensor in accordance with an exemplary embodiment of the present invention.

Referring now to FIG. 24, the dual-SRR sensor 116 in accordance with an exemplary embodiment is illustrated. In the illustrated embodiment, the regions 138, 140, 142 are representative of the selective areas where different sensing films may be disposed underneath the regions to control magnetic resonance of the SRR sensor and/or inductive coupling between different regions of the SRR sensor. The sensor selectivity may be increased due to the local swelling effect of the sensing film. The selective areas may be selectively used for controlling magnetic resonance separately. In some embodiments, for example, upper or lower portion of the outer conductive bands 124, 128 may be used selectively so as to control only the slit opening of the dual-SRR sensor 116.

In FIG. 24, in one embodiment, split ring 126 of the SRR sensor 116 may be provided with a dielectric sensing film in region 138 beneath, for levitating the one side 126 of SRR sensor in relation to other side 124 of SRR sensor by swelling the sensing film. In another embodiment, split ring 128 of the SRR sensor 116 may be provided with a dielectric sensing film in region 140 beneath, for levitating the one side of the ring in relation to other side of the ring sensor by swelling the sensing film in region 140. In another embodiment, split ring 130 of the SRR sensor 116 may be provided with a dielectric sensing film in region 142 beneath, for levitating the one side of the ring in relation to other side of the ring sensor by swelling the sensing film in region 142.

In addition to above discussed dual-split ring resonator structures, aspects of the present invention may be applied to individual split ring resonators, and other LCR resonators operating at different frequency ranges including radio-frequencies, microwave frequencies, and optical frequencies, to increase sensor selectivity.

In addition to discussed dual-split ring resonator structures, the exemplary techniques for increasing sensor selectivity may be applied to individual split ring resonators, microwave split-ring resonators, radio-frequency coils, and other LCR resonators. For example, in the optical range of the electromagnetic spectrum, the resonators may be approximately in the range of 10 to 1000 nanometers in size with simplified geometries.

Figure 25:
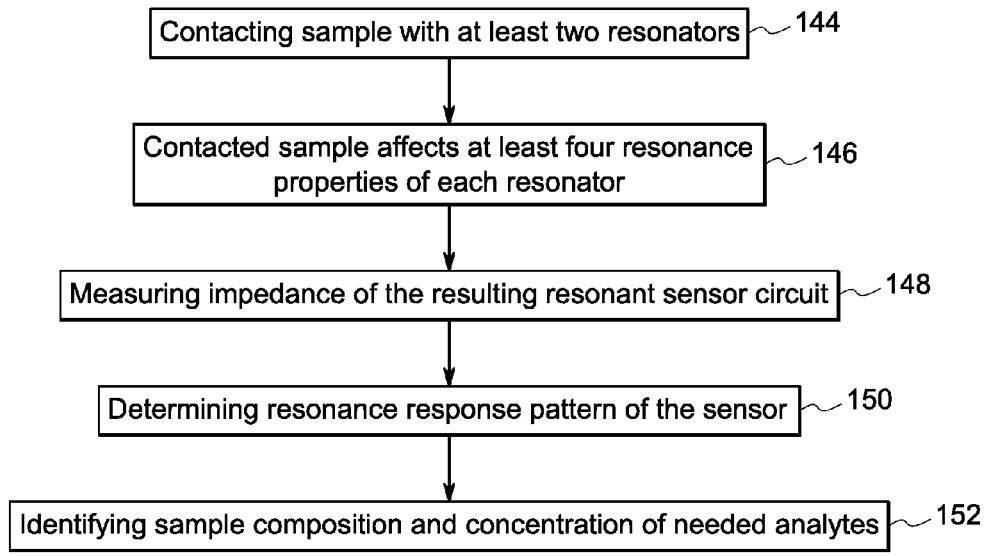
FIG. 25 is a flow chart illustrating exemplary steps involved in analyzing a sample in accordance with an exemplary embodiment of the present invention.

Referring to FIG. 25, a flow chart illustrating steps involved in analyzing a sample is disclosed. The method includes contacting an LCR sensor having at least two sensing elements, with a sample as represented by the step 144. In one embodiment, the LCR sensor includes a plurality of first sensing elements mutually spaced apart and disposed on the substrate, a plurality of second sensing elements; each second sensing element being disposed overlapping the corresponding first sensing element. An isolator is disposed between the corresponding first and second sensing elements. In a specific embodiment, the group of first and second sensing elements together form a coil structure. When a radio frequency field passes through the sensing coil structure, an AC voltage is generated across the sensing coil. In another embodiment, the sensing elements may be disposed on either sides of a substrate having a plurality of holes. In yet another embodiment, the sensing element may be a split ring resonant sensor. In another specific embodiment, the first and second sensing elements include optical LCR resonators.

In the LCR sensor, sensing response of each sensing element is provided from analyte-dependent change in circuit capacitance, analyte-dependent change in circuit resistance, analyte-dependent change in circuit inductance or a combination of the three as represented by the step 146. In other words, in accordance with the embodiments of the present technique, when the LCR sensor having at least two sensing elements coated with the same sensing material are contacted to a sample, the contacted sample affects at least four resonance properties of the sensor. The combination of changes in the capacitance, inductance, and resistance is measured by measuring frequency response spectrum of the LCR resonant sensing circuit as represented by the step 148. The analyte-induced changes in the sensing films of the sensing elements affect the impedance of the sensor circuit through the changes in circuit resistance and circuit capacitance.

The resonance response pattern of the spectrum is determined as represented by the step 150. The spectrum includes a real part (Zre) of the impedance spectrum, an imaginary part (Zim) of the impedance spectrum, frequency of the maximum of the real part of the impedance (Fp), peak magnitude of the real part of the impedance (Zp), peak frequency (F1) and magnitude (Z1) of the imaginary part of the impedance, and resonant frequency (F2) and magnitude (Z2) of the imaginary part of the impedance. The sample composition and concentration of the analyte are identified as represented by the step 152.

Figure 26:
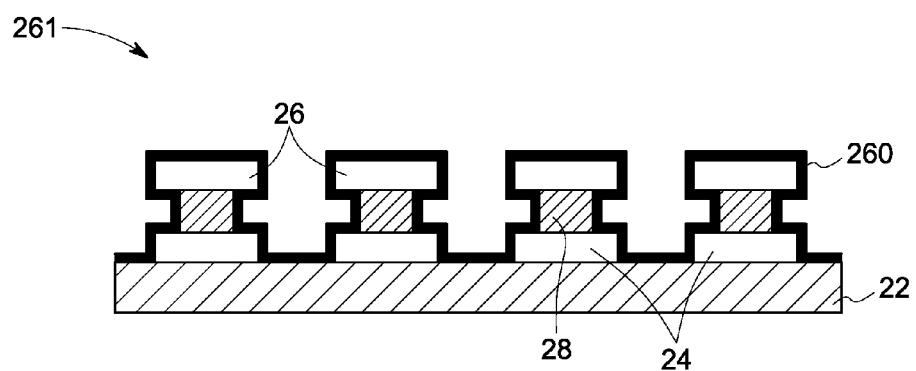
FIG. 26 is a sectional view of an electrode structure in accordance with an exemplary embodiment of the present invention.

Referring to FIG. 26, a section view of an electrode structure 261 in accordance with an exemplary embodiment of the present invention is shown. In the illustrated embodiment, a protecting film 260 is conformally applied onto the first sensing elements 24, the second sensing elements 26, the substrate 22, and the dielectric isolators 28. In an alternative embodiment, the protecting film 260 is conformally applied onto the first sensing elements 24 and the second sensing elements 26. As used herein, the term "conformally applied" refers to uniform application/coating of the protecting film 260 such that the protecting film 260 has a uniform thickness over all areas where it is applied to the sensing element 24, 26 and/or the dielectric isolator 28. A thickness of the protecting coating 260 is smaller than a dielectric gap (for example, the dielectric gap 30 the sensing coil structure 29 of FIG. 2).

While only certain features of the invention have been illustrated and described herein, many modifications and changes will occur to those skilled in the art. It is, therefore, to be understood that the appended claims are intended to cover all such modifications and changes as fall within the true spirit of the invention.

The invention claimed is:

1. A sensing system for selective analyte detection in presence of interferences, comprising:
  an inductor-capacitor-resistor (LCR) resonant sensor comprising:
    a substrate;
    a plurality of first sensing elements mutually spaced apart and disposed on the substrate;
    a plurality of second sensing elements, each second sensing element disposed overlapping a corresponding first sensing element of the plurality of second sensing elements; and
    a protecting film applied onto the plurality of first sensing elements and the plurality of second sensing elements, wherein the protecting film is disposed to be in a physical contact with the analyte and is configured to enable an operational contact of the plurality of first sensing elements and the plurality of second sensing elements with the analyte.

2. The sensing system of claim 1, wherein the protecting film is conformally applied to the plurality of first sensing elements and the plurality of second sensing elements.

3. The sensing system of claim 1, wherein the protecting film is configured to be inert to the analyte.

4. The sensing system of claim 1, wherein the protecting film is configured to allow penetration and transmission of an electromagnetic field generated between the plurality of first sensing elements and the plurality of second sensing elements into the analyte.

5. The sensing system of claim 1, wherein the (LCR) resonant sensor further comprises a plurality of dielectric isolators, each dielectric isolator being disposed between the corresponding first and second sensing elements.

6. The sensing system of claim 5, wherein the protecting film is non-conformally applied onto the plurality of first sensing elements, the plurality of second sensing elements, and the plurality of dielectric isolators such that the protecting film forms a uniform thickness on the substrate.

7. The sensing system of claim 6, wherein the protecting film has a height which is greater than a sum of a height of a corresponding first sensing element of the plurality of first sensing elements, a height of a corresponding second sensing element of the plurality of second sensing elements, overlapping the corresponding first sensing element, and a height of a corresponding dielectric isolator of the plurality of dielectric isolators, being disposed between the corresponding first sensing element and the corresponding second sensing element.

8. The sensing system of claim 5, wherein at least one of the substrate and the plurality of dielectric isolators have a dimensional property which is configured to change when the LCR resonant sensor interacts with the analyte.

9. The sensing system of claim 8, wherein the change in the dimensional property comprise at least one of swelling, shrinking, and bending.

10. The sensing system of claim 6, wherein at least one of the substrate and the plurality of dielectric isolators have a dielectric property which is configured to change when the LCR resonant sensor interacts with the analyte.

11. The sensing system of claim 5, wherein the protecting film is configured to prevent a direct physical contact of the plurality of first sensing elements, the plurality of second sensing elements and the plurality of dielectric isolators with the analyte.

12. The sensing system of claim 1, wherein the protecting film has a thickness which is smaller than a dielectric gap of a sensing coil structure formed using the plurality of first sensing elements and the plurality of second sensing elements.

13. The sensing system of claim 1, wherein the protecting film comprises at least one of a dielectric material, silicon dioxide, silicon nitride, silicon carbide, parylene, silicone, fluorinated polymers, ceramics, or a combination thereof.

14. The sensing system of claim 1, wherein each first sensing element has a first end coupled to one end of the corresponding second sensing element and a second end coupled to another end of the corresponding second sensing element.

15. The sensing system of claim 1, wherein the LCR resonant sensor further comprises a plurality of holes formed in the substrate, for enabling flow of the analyte through the holes, wherein the plurality of holes are disposed between the plurality of first sensing elements.

16. The sensing system of claim 15, wherein the LCR resonant sensor is a multivariable LCR resonant sensor; wherein an electric field distribution between the plurality of first sensing elements is substantially uniform along a plane of the plurality of first sensing elements and the plurality of holes.

17. A method for fabrication of an inductor-capacitor-resistor (LCR) resonant sensor, comprising:
   applying a plurality of first sensing elements on a substrate;
   applying at least one dielectric layer on the plurality of first sensing elements,
   applying a plurality of second sensing elements on the at least one dielectric layer, each second sensing element being disposed corresponding to position of each first sensing element such that the at least one dielectric layer is disposed between the plurality of first and second sensing elements; and
   applying a protecting film onto the plurality of first sensing elements and the plurality of second sensing elements, wherein the protecting film is disposed to be in a physical contact with an analyte and is configured to enable an operational contact of the plurality of first sensing elements and the plurality of second sensing elements with the analyte.

18. The method of claim 17, further comprising conformally applying the protecting film onto the plurality of first sensing elements and the plurality of second sensing elements.

19. The method of claim 17, further comprising non-conformally applying the protecting film onto the plurality of first sensing elements, the plurality of second sensing elements, and the at least one dielectric layer.

* * * * *